US010598625B2

(12) United States Patent
Crooks et al.

(10) Patent No.: US 10,598,625 B2
(45) Date of Patent: Mar. 24, 2020

(54) METHODS AND SYSTEMS FOR THE DETECTION OF ANALYTES

(71) Applicant: BOARD OF REGENTS, THE UNIVERSITY OF TEXAS SYSTEM, Austin, TX (US)

(72) Inventors: Richard M. Crooks, College Station, TX (US); Ian Richards, Austin, TX (US); Josephine Hofstetter, Austin, TX (US); Molly Kogan, Austin, TX (US); Yi-Ju Tsai, Austin, TX (US); Long Luo, Austin, TX (US)

(73) Assignee: Board of Regents, The University System of Texas, Austin, TX (US)

( * ) Notice: Subject to any disclaimer, the term of this patent is extended or adjusted under 35 U.S.C. 154(b) by 342 days.

(21) Appl. No.: 15/564,825

(22) PCT Filed: Apr. 8, 2016

(86) PCT No.: PCT/US2016/026665
§ 371 (c)(1),
(2) Date: Oct. 6, 2017

(87) PCT Pub. No.: WO2016/164738
PCT Pub. Date: Oct. 13, 2016

(65) Prior Publication Data
US 2018/0120250 A1     May 3, 2018

Related U.S. Application Data

(60) Provisional application No. 62/144,902, filed on Apr. 8, 2015.

(51) Int. Cl.
*G01N 27/327*     (2006.01)
*G01N 33/543*     (2006.01)
(Continued)

(52) U.S. Cl.
CPC ......... *G01N 27/3278* (2013.01); *G01N 27/26* (2013.01); *G01N 27/4161* (2013.01);
(Continued)

(58) Field of Classification Search
CPC .. G01N 27/3278; G01N 27/26; G01N 27/447; G01N 33/48; G01N 33/74;
(Continued)

(56) References Cited

U.S. PATENT DOCUMENTS 5,602,040 A    2/1997   May et al.
5,622,871 A    4/1997   May et al.
(Continued)

FOREIGN PATENT DOCUMENTS

AU     1705092     8/1992
EP     0234938     9/1987
(Continued)

OTHER PUBLICATIONS

S.R. Brankovic, et al. "Metal monolayer deposition by replacement of metal adlayers on electrode surfaces", Surface Science, 474(1-3): p. L173-L179, Mar. 2001.*
(Continued)

*Primary Examiner* — J. Christopher Ball
(74) *Attorney, Agent, or Firm* — Meunier Carlin & Curfman LLC

(57) ABSTRACT

Provided herein are methods and devices for the detection of analytes. The methods employ particles formed from a first metal conjugated to analytes. The analyte conjugated to the particle formed from the first metal can be accumulated at a working electrode. The first metal can be galvanically exchanged with ions of a second metal to form a layer of the first metal at the working electrode. The first metal can then be electrochemically detected and/or quantified. Using this method, analytes can be detected at low concentrations a few
(Continued)

femtomolar via anodic stripping voltammetry, with no washing steps or electrode modifications.

24 Claims, 11 Drawing Sheets

(51) Int. Cl.
| | |
|---|---|
| G01N 33/48 | (2006.01) |
| G01N 27/447 | (2006.01) |
| G01N 27/26 | (2006.01) |
| G01N 27/416 | (2006.01) |
| G01N 33/74 | (2006.01) |

(52) U.S. Cl.
CPC ........... *G01N 27/447* (2013.01); *G01N 33/48* (2013.01); *G01N 33/5438* (2013.01); *G01N 33/54306* (2013.01); *G01N 33/54313* (2013.01); *G01N 33/74* (2013.01); *G01N 2333/58* (2013.01)

(58) Field of Classification Search
CPC ......... G01N 33/54306; G01N 27/4161; G01N 33/5438; G01N 33/54313; G01N 2333/58
See application file for complete search history.

(56) References Cited

U.S. PATENT DOCUMENTS

| | | |
|---|---|---|
| 5,656,503 A | 8/1997 | May et al. |
| 5,705,402 A | 1/1998 | Leland et al. |
| 6,100,045 A | 8/2000 | Van Es |
| 7,109,042 B2 | 9/2006 | May et al. |
| 8,337,692 B2 | 12/2012 | Porter et al. |
| 8,852,826 B2 | 10/2014 | Vacchione et al. |
| 8,921,118 B2 | 12/2014 | Siegel et al. |
| 8,968,678 B2 | 3/2015 | Hu |
| 2001/0008774 A1 | 7/2001 | May et al. |
| 2003/0121788 A1 | 7/2003 | Gascoyne et al. |
| 2003/0186274 A1 | 10/2003 | Limoges et al. |
| 2007/0000776 A1 | 1/2007 | Karube et al. |
| 2007/0020699 A1 | 1/2007 | Carpenter et al. |
| 2007/0189921 A1 | 8/2007 | Duong et al. |
| 2007/0227248 A1 | 10/2007 | Glauser |
| 2008/0019866 A1 | 1/2008 | Paek et al. |
| 2009/0098662 A1 | 4/2009 | Birch et al. |
| 2010/0015633 A1 | 1/2010 | Lu et al. |
| 2010/0320092 A1 | 12/2010 | Porter et al. |
| 2011/0111517 A1 | 5/2011 | Siegel et al. |
| 2011/0118139 A1 | 5/2011 | Metha et al. |
| 2011/0123398 A1 | 5/2011 | Carrilho et al. |
| 2012/0121481 A1 | 5/2012 | Romanowsky et al. |
| 2014/0251832 A1 | 9/2014 | Porter |
| 2015/0132742 A1 | 5/2015 | Thuo et al. |
| 2015/0355132 A1 | 12/2015 | Crooks et al. |
| 2016/0327510 A1 | 11/2016 | Crooks et al. |
| 2017/0173578 A1 | 6/2017 | Crooks et al. |

FOREIGN PATENT DOCUMENTS

| | | |
|---|---|---|
| EP | 0859229 | 8/1998 |
| GR | 3034325 | 12/2000 |
| KR | 10-2011-0028019 | 3/2011 |
| WO | 1991001005 | 1/1991 |
| WO | 2009068862 | 6/2009 |
| WO | 2009121037 | 10/2009 |
| WO | 2010102279 | 9/2010 |
| WO | 2010102294 | 9/2010 |
| WO | 2011000047 | 1/2011 |
| WO | 2013036617 | 3/2013 |
| WO | 2013158827 | 10/2013 |
| WO | 2014031523 | 2/2014 |
| WO | 2015102937 | 7/2015 |
| WO | 2016164738 | 10/2016 |

OTHER PUBLICATIONS

Extended European Search Report dated Dec. 5, 2018, from related EP Application No. 16777366.2, 13 pages.
Scida, K. et al. "Simple, Sensitive, and Quantitative Electrochemical Detection Method for Paper Analytical Devices", Analytical Chemistry, vol. 86, No. 13, Jul. 1, 2014, pp. 6501-6507.
Cunningham, C.J. et al, "Paper diagnostic device for quantitative electrochemical detection of ricin at picomolar levels", Lab on a Chip, vol. 15, No. 18, Jan. 1, 2015, pp. 3707-3715.
Oh, J. et al. "Recent developments in electrochemical paper-based analytical devices", Analytical Methods, vol. 7, No. 19, Jan. 1, 2015, pp. 7951-7960.
Zhang, B. et al. "Anodic-Stripping Voltammetric Immunoassay for Ultrasensitive Detection of Low-Abundance Proteins Using Quantum Dot Aggregated Hollow Microspheres", Chemistry—a European Journal, vol. 19, No. 7, Jan. 4, 2013, pp. 2496-2503.
Communication pursuant to Rule 164(1) EPC dated Aug. 31, 2018, from European Application No. 16777366.2, 16 pages.
Amatore et al. "Theory and Experiments of Transport at Channel Microband Electrodes under Laminar Flows. 1. Steady-State Regimes at a Single Electrode." Anal. Chem. 2007, 79, 8502-8510.
Amatore et al. "Using electrochemical coupling between parallel microbands for in situ monitoring of flow rates in microfluidic channels." J. Electroanal. Chem. 2004, 573, 333-343.
Anicet et al. "Electron Transfer in Organized Assemblies of Biomolecules. Step-by-Step Avidin/Biotin Construction and Dynamic Characteristics of a Spatially Ordered Multilayer Enzyme Electrode." J. Phys. Chem. B 1998, 102, 9844-9849.
Apilux et al. "Development of automated paper-based devices for sequential multistep sandwich enzyme-linked immunosorbent assays using inkjet printing." Lab Chip 2013, 13, 126-135.
Authier et al. "Gold Nanoparticle-Based Quantitative Electrochemical Detection of Amplified Human Cytomegalovirus DNA Using Disposable Microband Electrodes." Anal. Chem., 2001, 73, 4450-4456.
Bahrami et al. "Pressure Drop of Fully Developed, Laminar Flow in Rough Microtubes." J. Fluids Eng. 2005, 128, 632-637.
Bettencourt et al. "N-Terminal-Pro-Brain Natriuretic Peptide Predicts Outcome After Hospital Discharge in Heart Failure Patients." Circulation 2004, 2168-2174.
Carrilho et al. "Paper Microzone Plates." Anal. Chem. 2009, 81, 5990-5998.
Carrilho et al. "Understanding wax printing: A simple micropatterning process for paper-based microfluidics." Anal Chem 2009, 81, 7091-7095.
Carvalhal et al. "Electrochemical-Detection in a Paper-Based Separation Device." Anal. Chem. 2010, 82, 1162-1165.
Cate et al. "Simple, distance-based measurement for paper analytical devices" Lab Chip. 2013, 13, 2397-2404.
Chaudhry et al. "Patterns of Weight Change Preceding Hospitalizations for Heart Failure." Circulation, 2007, 116, 1549-1554.
Cheng et al. "Paper-based ELISA." Angewandte Chemie International Edition English 2010, 49(28), 4771-4774.
Choi et al "Microfluidic-based biosensors toward point-of-care detection of nucleic acids and protiens," Microfluidics and Nanofluidics, 2010, 10(2), 231-247.
Compton et al. "Double-channel electrodes. Beyond the Leveque Approximation." J. Chem. Soc. Farad. T. Jan. 1988, 84, 4359-4367.
Cunningham et al. "Paper-Based Sensor for Electrochemical Detection of Silver Nanoparticle Labels by Galvanic Exchange." ACS Sens. 2016, 1(1), 40-47.
Daniels et al. "Natriuretic Peptides." J. Am. Coll. Cardiol. 2007, 50, 12.
Dash et al. "Oxidation by Permanganate: Synthetic and Mechanistic Aspects." Tetrahedron, 2009, 65, 707-739.
Delaney et al. "Electrogenerated Chemiluminescence Detection in Paper-Based Microfluidic Sensors." Anal. Chem. 2011, 83, 1300-1306.
Di Angelantonio et al. "Association of Cardiometabolic Multimorbidity With Mortality." JAMA 2015, 314, 52-60.
Dickstein et al. "ESC Guidelines for the Diagnosis and Treatment of Acute and Chronic Heart Failure." Eur. Heart J. 2008, 29, 54.

(56) References Cited

OTHER PUBLICATIONS

Dungchai et al. "Electrochemical Detection for Paper-Based Microfluidics." Anal. Chem. 2009, 81, 5821-5826.
Escosura-Muniz et al. "Size-Dependent Direct Electrochemical Detection of Gold Nanoparticles: Application in Magnetoimmunoassays." Nanoscale, 2011, 3, 3350-3356.
Fanjul-Bolado et al. "Electrochemical characterization of screen-printed and conventional carbon paste electrodes." Electrochim. Acta 2008, 53, 3635-3642.
Feng et al. "Using Nanostructured Conductive Carbon Tape Modified with Bismuth as the Disposable Working Electrode for Stripping Analysis in Paper-Based Analytical Devices." Talanta 2013, 115, 235-240.
Fenton et al. "Multiplex Lateral-Flow Test Strips Fabricated by Two-Dimensional Shaping." ACS Appl. Mater. Interfaces, 2009, 1(1), 124-129.
Fu et al. "Chemical Signal Amplification in Two-Dimensional Paper Networks." Sens. Actuators B Chem., 2010, 149, 325-328.
Fu et al. "Controlled reagent transport in disposable 2D paper networks." Lab Chip 2010, 10, 918-20.
Ge et al. "A Disposable Immunosensor Device for Point-of-Care Test of Tumor Marker Based on Copper-Mediated Amplification." Biosens. Bioelectron, 2013, 43, 425-431.
Ge et al. "Photoelectrochemical Lab-on-Paper Device Based on an Integrated Paper Supercapacitor and Internal Light Source." Anal. Chem., 2013, 85, 3961-3970.
Glavan et al. "Rapid Fabrication of Pressure-Driven Open-Channel Microfluidic Devices in Omniphobic RF Paper." Lab Chip, 13(15), 2922-2930.
Go et al. "Heart Disease and Stroke Statistics—2013 Update." Circulation 2013, 127, e6-e245.
Govindajaran et al. "A low cost point-of-care viscous sample preparation device for molecular diagnosis in the developing world; an example of microfluidic origami." Lap Chip, 2011, 12, 174-181.
Gubala et al. "Point of Care Diagnostics: Status and Future." Anal. Chem., 2011, 84, 487-515.
Hu et al. "Advances in Paper-Based Point-of-Care Diagnostics." Biosens. Bioelectron. 2014, 54, 585-597.
Iqbal et al. "Cardiac Biomarkers: New Tools for Heart Failure Management." Cardiovasc. Diagn. Ther. 2012, 2, 147-164.
Januzzi et al. "Use of Aminoterminal Pro-B-Type Natriuretic Peptide to Guide Outpatient Therapy of Patients With Chronic Left Ventricular Systolic Dysfunction." J. Am. Coll. Cardiol. 2011, 58, 1881-1889.
Jencks et al. "Rehospitalizations among Patients in the Medicare Fee-for-Service Program." N. Engl. J. Med. 2009, 360, 11.
Kartalov et al. "Microfluidic vias enable nested bioarrays and autoregulatory devices is Newtonian fluids." PNAS, 2006, 103(33), 12280-12284.
Kenis et al. "Fabrication inside Microchannels Using Fluid Flow." Acc. Chem. Res. 2000, 33, 841-847.
Laschi et al. "A new gravity-driven microfluidic-based electrochemical assay coupled to magnetic beads for nucleaic acid detection." Proteomics, 2010, 31(22), 3727-3736.
Laschi et al. "Development of disposable low density screen-printed electrode arrays for simultaneous electrochemical measurements of the hybridisation reaction." J. Electroanal. Chem. 2006, 593, 211-218.
Lesniewski et al. "Antibody Modified Gold Nanoparticles for Fast and Selective, Colorimetric T7 Bacteriophage Detection", Bioconj. Chem. 2014, 25, 644-648.
Lewis et al. "Point-of-Care Assay Platform for Quantifying Active Enzymes to Femtomolar Levels Using Measurements of Time as the Readout." Anal. Chem., 2013, 85, 10432-10439.
Lewis et al. "Quantifying Analytes in Paper-Based Microfluidic Devices Without Using External Electronic Readers." Angew. Chem., Int. Ed. 2012, 51, 12707-12710.
Li et al. "A Perspective on Paper-Based Microfluidics: Current Status and Future Trends." Biomicrofluidics, 2012, 6, 011301.
Licht et al. "Time and Spatial Dependence of the Concentration of Less Than $10^5$ Microelectrode-Generated Molecules." Science 1989, 243, 1176-1178.
Liu et al. "Aptamer-Based Origami Paper Analytical Device for Electrochemical Detection of Adenosine." Angew. Chem. Int. Ed., 2012, 51, 6925-6928.
Liu et al. "Paper-Based Electrochemical Sensing Platform with Integral Battery and Electrochromic Read-Out." Anal. Chem. 2012, 84, 2528-2532.
Liu et al. "Paper-Based SlipPAD for High-Throughput Chemical Sensing." Anal. Chem. 2013, 85, 4263-4267.
Liu et al. "Three-Dimensional Paper Microfluidic Devices Assembled Using the Principles of Origami." J. Am. Chem. Soc. 2011, 133, 17564-17566.
Liu et al., "Disposable Electrochemical Immunosensor Diagnosis Device Based on Nanoparticle Probe and Immunochromatographic Strip", Anal. Chem. 2007, 79, 7644-7653.
Livnah et al. "Three-dimensional structures of avidin and the avidin-biotin complex." Proc. Natl. Acad. Sci. 1993, 90, 5076-5080.
Lu et al. "Electrochemical DNA Sensor Based on Three-Dimensional Folding Paper Device for Specific and Sensitive Point-of-Care Testing." Electrochimica Acta, 2012, 80, 334-341.
Lu et al. "Rapid prototyping of paper-based microfluidics with wax for low cost, portable bioassay." Electrophoresis, 2009, 30, 1497-1500.
Lutz et al. "Two-dimensional paper networks: programmable fluidic disconnects for multi-step processes in shaped paper." Lab Chip 2011, 11, 4274-8.
Martinez et al. "Diagnostics for the Developing World: Microfluidic paper-based analytical devices." Anal Chem 2010, 82, 3-10.
Martinez et al. "Flash: A rapid method for prototyping paper-based microfluidic devices." Lab Chip Dec. 2008, 8(12), 2146-2150.
Martinez et al. "Patterned Paper as a Platform for Inexpensive, Low-Volume, Portable Bioassays." Angew. Chem., Int. Ed. 2007, 46, 1318-1320.
Martinez et al. "Programmable diagnostic devices made from paper and table." Lab chip, 2010, 10, 2499-2504.
Martinez et al. "Three-dimensional microfluidic devices fabricated in layered paper and tape." PNAS, 2008, 105(50), 1906-19611.
Maxwell et al. "Paper-Based Electroanalytical Devices for Accessible Diagnostic Testing." MRS Bull., 2013, 38, 309-314.
McCullough et al. "B-Type Natriuretic Peptides: A Diagnostic Breakthrough for Clinicians." Rev. Cardiovasc. Med. 2003, 4, 72-80.
Nery et al. "Sensing approaches on paper-based devices: a review." Anal. Bioanal. Chem. 2013, 405, 7573-95.
Niavarani et al. "The effective slip length and vortex formation in laminar flow over a rough surface." Phys. Fluids 2009, 21, 052105-10.
Nie et al. "Electrochemical sensing in paper-based microfluidic devices." Lab Chip 2010, 10, 477-483.
Nie et al. "Integration of paper-based microfluidic devices with commercial electrochemical readers." Lap Chip 2010, 10(22), 3163-3169.
Osborn et al. "Microfluidics without pumps: reinventing the T-sensor and H-filter in paper networks." Lap Chip, 2010, 10, 2659-2665.
Parolo et al. "Paper-based nanobiosensors for diagnostics." Chem. Soc. Rev. 2013, 42, 450-457.
Pelton "Bioactive Paper Provides a Low-Cost Platform for Diagnostics." TrAC Trends Anal. Chem., 2009, 28, 925-942.
Phares et al. "A study of laminar flow of polar liquids through circular microtubes." Phys. Fluids 2004, 16, 1267-1272.
Putnam. Composition and Concentrative Properties of Human Urine, NASA, 1971.
Renault et al. "Electrochemistry in Hollow-Channel Paper Analytical Devices." JACS, 2014, 136(12), 4616-4623.
Renault et al. "Hollow-channel paper analytical devices." Analytical Chemistry, 2013, 85, 7976-7979.
Renault et al. "Three-Dimensional Wax Patterning of Paper Fluidic Devices." Langmuir 2014, 30, 7030-7036.
Roh et al. "Rapid, Reversible Preparation of Size-Controllable Silver Nanoplates by Chemical Redox." Langmuir, 2010, 26, 11621-11623.

(56) References Cited

OTHER PUBLICATIONS

Rowe et al. "CheapStat: An Open-Source, "Do-It-Yourself" Potentiostat for Analytical and Educational Applications." PLoS One, 2011, 6, e23783.
Ruecha et al. "Novel Paper-Based Cholesterol Biosensor Using Graphene/polyvinylpyrrolidone/polyaniline Nanocomposite." Biosens. Bioelectron., 2014, 52, 13-19.
Sabatine et al. "Complementary Roles for Biomarkers of Biomechanical Strain ST2 and N-Terminal Prohormone B-Type Natriuretic Peptide in Patients With ST-Elevation Myocardial Infarction." Circulation 2008, 117, 1936-1944.
Schilling et al. "Fully enclosed microfluidic paper-based analytical devices." Anal. Chem. 2012, 84(3), 1579-1585.
Scida et al. "DNA Detection Using Origami Paper Analytical Devices." Analytical Chemistry, 2013, 85(20), 9713-9720.
Scida et al., "Simple, Sensitive, and Quantitative Electrochemical Detection Method for Paper Analytical Devices", Anal. Chem., 2014, 86, 6502-6504.
Seong et al. "Efficient Mixing and Reactions within Microfluidic Channels Using Microbead-Supported Catalysts." J. Am. Chem. Soc. 2002, 124, 13360-13361.
Siegel et al. "Foldable Printed circuit boards on paper substrates." Adv Funct Mater, 2010, 20, 28-35.
Sonnichsen et al. "A Molecular Ruler Based on Plasmon Coupling of Single Gold and Silver Nanoparticles." Nat Biotech, 2005, 23, 741-745.
Szymanski et al. "Preparation and Quality Control of Silver Nanoparticle-antibody Conjugate for Use in Electrochemical Immunoassays." J. Immunol. Methods, 2013, 387, 262-269.
Szymanski et al. "Electrochemical Dissolution of Silver Nanoparticles and Its Application in Metalloimmunoassay", Electroanalysis. 2010, 22, 191-198.
Thom et al. "Fluidic batteries' as low-cost sources of power in paper-based microfluidic devices." Lab Chip 2012, 12, 1768-1770.
Troughton et al. "Treatment of Heart Failure Guided by Plasma Aminoterminal Brain Natriuretic Peptide (N-BNP) Concentrations." Lancet 2000, 1126-1130.
Unger et al. "Monolithic Microfabricated valves and pumps by Multilayer Soft Lithography." Science, 2000, 288, 113.
Waldo et al. "Pro-B-Type Natriuretic Peptide Levels in Acute Decompensated Heart Failure." J. Am. Coll. Cardiol. 2008, 51, 9.
Wang et al. "Paper-based three-dimensional electrochemical immunodevice based on multi-walled carbon nanotubes functionalized paper for sensitive point-of-care testing." Biosens. Bioelectron. 2012, 32, Abstract 238-243.
Wang et al. "Performance of screen-printed carbon electrodes fabricated from different carbon inks." Electrochim. Acta 1998, 43, 3459-3465.
Wang et al. "Electrochemical immunoassay for subgroup J of avian leukosis viruses using a glassy carbon electrode modified with a film of poly (3-thiophene boronic acid), gold nanoparticles, graphene and immobilized antibody", Micochimica Acta, 2012, 179, 227-234.
Wilson et al. "Standardization of Metalloimmunoassay Protocols for Assessment of Silver Nanoparticle Antibody Conjugates." J. Immunol. Methods 2013, 387, 303-307.
Wu et al. "Paper-Based Microfluidic Electrochemical Immunodevice Integrated with Nanobioprobes onto Graphene Film for Ultrasensitive Multiplexed Detection of Cancer Biomarkers." Anal. Chem., 2013, 85, 8661-8668.
Wu et al. "A Paper-Based Microfluidic Electrochemical Immunodevice Integrated with Amplification-by-Polymerization for the Ultrasensitive Multiplexed Detection of Cancer Biomarkers." Biosens. Bioelectron., 2014, 52, 180-187.
Xiang et al. "Using personal glucose meters and functional Dna sensors to quantify a variety of analytical targets." Nature Chemistry, 2011, 3, 697-703.
Yancy et al. "2013 ACCF/AHA Guideline for the Management of Heart Failure." J. Am. Coll. Cardiol. 2013, 62, 147-240.
Yang et al. "Integrated separation of blood plasma from whole blood for microfluidic paper-based analytical devices." Lab Chip 2012, 12, 274-80.
Yetisen et al. "Paper-based microfluidic point-of-care diagnostic devices." Lab Chip 2013, 13, 2210-2251.
Yu et al. "Microfluidic paper-based chemiluminescence biosensor for simultaneous determination of glucose and uric acid." Lab Chip 2011, 11, 1286-91.
Zhao et al. "Dual amplification strategy of highly sensitive thrombin amperometric aptasensor based on chitosan-Au nanocomposites." Analyst 2012, 137, 3488-3495.
Zhi-Xin et al. "Experimental Study on Flow Characteristics of Liquid in Circular Microtubes." Microscale Therm. Eng. 2003, 7, 253.
Zogo et al. "Influence of Pre-Oxidation with Potassium Permanganate on the Efficiency of Iron and Manganese Removal from Surface Water by Coagulation-Flocculation Using Aluminium Sulphate: Case of the Okpara Dam in the Republic of Benin." J. Environ. Chem. Ecotoxicol., 2011, 3, 1-8.
International Search Report and Written Opinion dated Jun. 11, 2015 in related International Application PCT/US2015/020569.
International Search Report and Written Opinion issued in Application No. PCT/US2016/026665, dated Aug. 22, 2016.
International Search Report and Written Opinion issued in Application No. PCT/US14/71389, dated May 22, 2015.
International Preliminary Report on Patentability dated Oct. 21, 2014 in related International Application PCT/US2013/037082.
International Search Report/Written Opinion dated Aug. 12, 2013 in related International Application No. PCT/US2013/037082.
Extended European Search Report dated Jul. 28, 2017 in related European Application 14876429.3.
Extended European Search Report dated Oct. 22, 2015 in related European Application 13778902.
Restriction Requirement dated Sep. 22, 2017 in related U.S. Appl. No. 15/109,746.
Non-Final Office Action dated Dec. 15, 2016 in related U.S. Appl. No. 13/658,352.
Notice of Allowance dated Jun. 22, 2017 in related U.S. Appl. No. 13/865,352.

\* cited by examiner

METHODS AND SYSTEMS FOR THE DETECTION OF ANALYTES

CROSS-REFERENCE TO RELATED APPLICATIONS

This application is a 371 U.S. National Stage of International Application No. PCT/US2016/026665, filed Apr. 8, 2016, which claims benefit of U.S. Provisional Application No. 62/144,902, filed Apr. 8, 2015, each of which are hereby incorporated herein by reference in their entireties.

STATEMENT REGARDING FEDERALLY SPONSORED RESEARCH

This invention was made with government support under Grant No. HDTRA1-13-1-0031 awarded by the Department of Defense/Defense Threat Reduction Agency (DTRA). The government has certain rights in the invention.

BACKGROUND

There is a significant interest in the development of paper point-of-care (POC) devices that are cheap, user friendly, robust, sensitive, and portable. Such devices pose an effective solution to the existing economic and healthcare accessibility problems in underdeveloped countries, as well as the growing trend in more affluent societies to become better informed in terms of their health. Although commercial paper-based sensors have been around for about 25 years (e.g., pregnancy test and glucose test strips), few paper POC devices have been successfully commercialized. Such failure to produce trustworthy paper POC devices is a combination of many factors, including poor limits of detection (LOD), high non-specific adsorption (NSA), unstable reagents, long analysis time, complex user-technology interfaces, technically demanding detection method, and poor sensitivity.

SUMMARY

Provided herein are methods for the detection of analytes. The methods employ a robust electrochemical process, galvanic exchange, to facilitate the detection of analytes.

Methods for detecting analytes by galvanic exchange can comprise providing an analyte conjugated to a particle formed from a first metal, galvanically exchanging the first metal with ions of a second metal, thereby forming a product of the galvanic exchange, and detecting the product of the galvanic exchange (and by extension the analyte).

The product of the galvanic exchange can be detected by any suitable means. For example, in some cases, the product of the galvanic exchange can comprise a plurality of particles formed from the second metal. Forming the plurality of particles from the second metal can, in some examples, result in a color change, which can be spectroscopically measured and/or visibly observed to detect the product of the galvanic exchange (and by extension the analyte). In some cases, the analyte conjugated to the particle formed from the first metal can be provided at a working electrode, and the product of the galvanic exchange can comprise a layer of the first metal formed at the working electrode. In these embodiments, detecting the product of the galvanic exchange can comprise electrochemically detecting the first metal (and by extension the analyte).

Methods can further comprise providing ions of the second metal (e.g., by adding a compound comprising the second metal, such as a salt of the second metal, or electrochemically oxidizing a layer of the second metal present at the working electrode to provide ions of the second metal). These methods can be performed in conjunction with standard immunoassays to facilitate the detection/quantification of analytes of interest.

In some embodiments, methods for detecting an analyte can comprise providing an analyte conjugated to a particle formed from a first metal (i.e., an analyte conjugate) at a working electrode, and galvanically exchanging the first metal with ions of a second metal. For example, methods can comprise flowing fluid along a channel to accumulate an analyte conjugate in a region of the channel in electrochemical contact with a working electrode. The channel can be, for example, a microfluidic channel.

The analyte conjugate can be accumulated in the region of the channel in electrochemical contact with the working electrode by a localization element. The localization element can be any feature that is configured to increase the concentration of the analyte conjugate in the region of the channel in electrochemical contact with the working electrode in the presence of fluid flow through the channel. For example, the localization element can be a physical barrier disposed in the region of the channel in electrochemical contact with the working electrode (e.g., a material configured to physically entrap the analyte conjugate), one or more localization electrodes configured to apply an electric field to the region of the channel in electrochemical contact with the working electrode (e.g., configured to electrophoretically localize the analyte conjugate), a magnet configured to apply a magnetic field in the region of the channel in electrochemical contact with the working electrode, or a combination thereof.

The working electrode can, for example, comprise a second metal (e.g., a layer of the second metal), wherein the second metal has a higher reduction potential than the first metal. Once the analyte conjugate is accumulated in the region of the channel in electrochemical contact with the working electrode comprising the second metal (e.g., a layer of the second metal), the potential applied at the working electrode can be varied to oxidize the second metal at the working electrode to ions of the second metal. The ions of the second metal can galvanically exchange with the particles of the first metal, forming a plurality of particles of the second metal and ions of the first metal. The ions of the first metal can then be electrodeposited onto the working electrode (e.g., a layer of the first metal can be formed at the working electrode). The layer of the first metal (and by extension the analyte) can then be electrochemically detected and/or quantified, for example, using the working electrode (e.g., by anodic stripping voltammetry).

Also provided are devices for the electrochemical detection of analytes. The devices can comprise a channel defining a path for fluid flow from a fluid inlet to a fluid outlet, a working electrode positioned in electrochemical contact with a region of the channel, and a localization element configured to accumulate the analyte conjugate in the region of the channel in electrochemical contact with the working electrode. The working electrode can, for example, comprise a second metal (e.g., a layer of the second metal), wherein the second metal can have a higher reduction potential than the first metal.

Also provided are devices comprising a channel defining a path for fluid flow from a fluid inlet to a fluid outlet, a working electrode positioned in electrochemical contact with a region of the channel, a localization element configured to accumulate the analyte conjugate in the region of the channel in electrochemical contact with the working electrode, and an engageable platform that can be translocated to provide ions of a second metal to the region of the channel.

As described above, the localization element can be any feature that is configured to increase the concentration of the analyte conjugate in the region of the channel in electrochemical contact with the working electrode in the presence of fluid flow through the channel. For example, the localization element can be a physical barrier disposed in the region of the channel in electrochemical contact with the working electrode, one or more localization electrodes configured to apply an electric field to the region of the channel in electrochemical contact with the working electrode, a magnet configured to apply a magnetic field in the region of the channel in electrochemical contact with the working electrode, or a combination thereof.

In certain embodiments, the localization element can comprise a magnet configured to apply a magnetic field in the region of the channel in electrochemical contact with the working electrode. In these embodiments, the devices can comprise a channel defining a path for fluid flow from a fluid inlet to a fluid outlet, an electrode positioned in electrochemical contact with a region of the channel, and a magnet configured to apply a magnetic field to the region of the channel positioned in electrochemical contact with the electrode.

The devices and methods described herein are inexpensive, user friendly (e.g., they can provide for electrochemical detection without any washing steps or electrode modification), sensitive, portable, robust (they employ metal particles for signal amplification as opposed to enzymes), efficient, rapid, and can detect low concentrations (e.g., low picomolar to low femtomolar concentrations of analyte). As such, the device and methods are well suited for use in numerous applications including point-of-care (POC) diagnostics.

DETAILED DESCRIPTION

Figure 1:
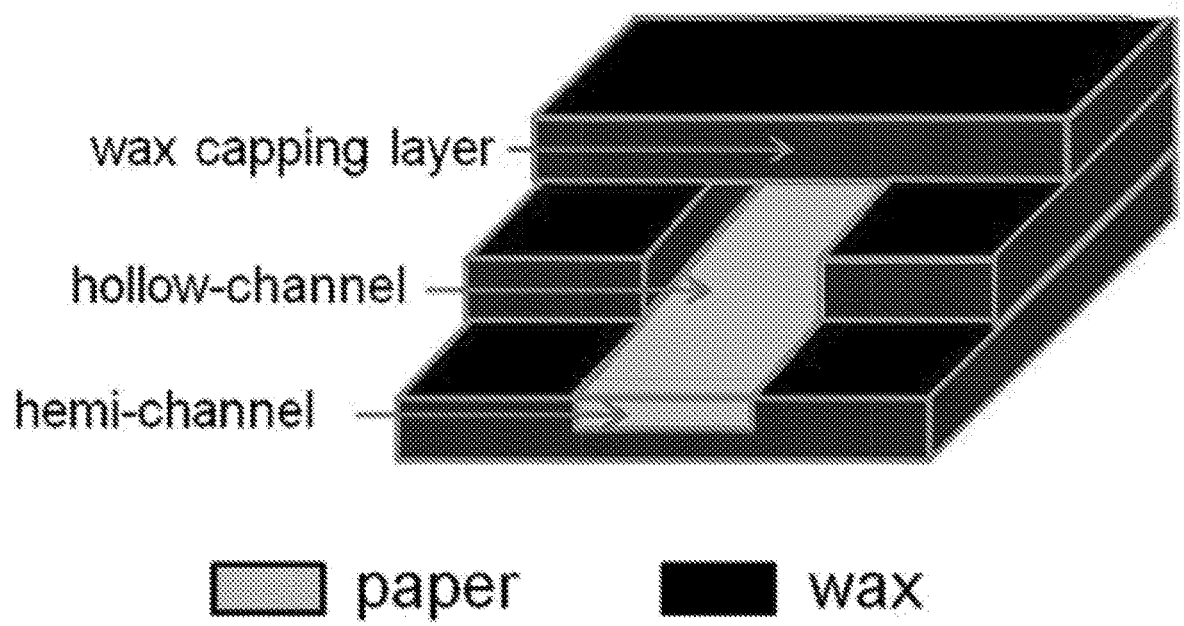
FIG. 1 is a schematic three-dimensional view of an example of a hollow channel comprising a hemichannel.

The methods and devices described herein may be understood more readily by reference to the following detailed description of specific aspects of the disclosed subject matter, figures and the examples included therein.

Before the present devices and methods are disclosed and described, it is to be understood that the aspects described below are not intended to be limited in scope by the specific devices and methods described herein, which are intended as illustrations. Various modifications of the devices and methods in addition to those shown and described herein are intended to fall within the scope of that described herein. Further, while only certain representative devices and method steps disclosed herein are specifically described, other combinations of the devices and method steps also are intended to fall within the scope of that described herein, even if not specifically recited. Thus, a combination of steps, elements, components, or constituents may be explicitly mentioned herein or less, however, other combinations of steps, elements, components, and constituents are included, even though not explicitly stated.

The term "comprising" and variations thereof as used herein is used synonymously with the term "including" and variations thereof and are open, non-limiting terms. Although the terms "comprising" and "including" have been used herein to describe various examples, the terms "consisting essentially of" and "consisting of" can be used in place of "comprising" and "including" to provide for more specific examples of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

As used in the description and the appended claims, the singular forms "a," "an," and "the" include plural referents unless the context clearly dictates otherwise. Thus, for example, reference to "a composition" includes mixtures of two or more such compositions, reference to "an agent" includes mixtures of two or more such agents, reference to "the component" includes mixtures of two or more such components, and the like.

"Optional" or "optionally" means that the subsequently described event or circumstance can or cannot occur, and that the description includes instances where the event or circumstance occurs and instances where it does not.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

Methods

Provided herein are methods for the detection of analytes. The methods employ particles formed from a first metal (e.g., nanoparticles formed from a first metal) conjugated to analytes. The particles formed from the first metal can serve as an electrochemical label for the analyte to which they are conjugated. Galvanically exchanging the first metal with ions of a second metal can form a product of the galvanic exchange. The product of the galvanic exchange can then be detected and/or quantified using any suitable method.

In some cases, the product of the galvanic exchange can comprise a plurality of particles formed from the second metal. Forming the plurality of particles from the second metal can, in some examples, result in a color change, which can be spectroscopically measured and/or visibly observed to detect the product of the galvanic exchange (and by extension the analyte). In some cases, the analyte conjugated to the particle formed from the first metal can be provided at a working electrode, and the product of the galvanic exchange can comprise a layer of the first metal formed at the working electrode. In these embodiments, detecting the product of the galvanic exchange can comprise electrochemically detecting the first metal (and by extension the analyte). Using these methods, analytes can be detected at low concentrations (e.g., low picomolar to low femtomolar concentrations of analyte) via anodic stripping voltammetry, with no washing steps or electrode modifications.

Methods can further comprise providing ions of the second metal (e.g., by adding a compound comprising the second metal, such as a salt of the second metal, or electrochemically oxidizing a layer of the second metal present at the working electrode to provide ions of the second metal, as discussed in more detail below). These methods can be performed in conjunction with standard immunoassays to facilitate the detection/quantification of analytes.

In some examples, methods for detecting an analyte can comprise providing (e.g., accumulating) an analyte conjugate at a working electrode. For example, in some cases, methods for detecting an analyte can comprise flowing fluid along a channel to accumulate an analyte conjugate in a region of the channel in electrochemical contact with a working electrode. The channel can be, for example, a microfluidic channel. The sensitivity of the detection methods can be improved by selectively localizing the analyte conjugate in the vicinity of the working electrode. For example, the analyte conjugate can be accumulated in the region of the channel in electrochemical contact with a working electrode by a localization element.

The localization element can be any feature that is configured to increase the concentration of the analyte conjugate in the region of the channel in electrochemical contact with the working electrode in the presence of fluid flow through the channel. For example, the localization element can be a physical barrier disposed in the region of the channel in electrochemical contact with the working electrode (e.g., a material configured to physically entrap the analyte conjugate), one or more localization electrodes configured to apply an electric field to the region of the channel in electrochemical contact with the working electrode (e.g., configured to electrophoretically localize the analyte conjugate), a magnet configured to apply a magnetic field in the region of the channel in electrochemical contact with the working electrode, or a combination thereof.

In certain cases, as discussed in more detail below, the working electrode can comprise a second metal (e.g., a layer of a second metal), wherein the second metal has a higher reduction potential than the first metal (e.g., the second metal is more noble than the first metal). In these cases, once the analyte conjugate is accumulated in the region of the channel in electrochemical contact with the working electrode comprising the second metal (e.g., a layer of the second metal), the potential applied at the working electrode can be varied to oxidize the second metal at the working electrode to ions of the second metal. The ions of the second metal can galvanically exchange with the particles of the first metal, which can form a plurality of particles of the second metal and ions of the first metal. A reducing potential can be applied to the working electrode resulting in electrodeposition of the ions of the first metal onto the working electrode (e.g., a layer of the first metal can be formed at the working electrode). The layer of the first metal (and by extension the analyte) can then be electrochemically detected and/or quantified, for example, using the working electrode.

The analyte can be, for example, an antibody, peptide (natural, modified, or chemically synthesized; e.g. a natriuretic peptide), protein (e.g., a glycoprotein, a lipoprotein, or a recombinant protein), polynucleotide (e.g., DNA or RNA, an oligonucleotide, an aptamer, or a DNAzyme), lipid, polysaccharide, small molecule organic compound (e.g., a hormone, a prohormone, a narcotic, or a small molecule pharmaceutical), pathogen (e.g., bacteria, virus, or fungi, or protozoa), or combination thereof.

In some embodiments, the analyte can be a molecule of interest present in a fluid sample that is introduced into the channel. By way of example, the fluid sample can be a bodily fluid. "Bodily fluid", as used herein, refers to a fluid composition obtained from or located within a human or animal subject. Bodily fluids include, but are not limited to, urine, whole blood, blood plasma, serum, tears, semen, saliva, sputum, exhaled breath, nasal secretions, pharyngeal exudates, bronchoalveolar lavage, tracheal aspirations, interstitial fluid, lymph fluid, meningeal fluid, amniotic fluid, glandular fluid, feces, perspiration, mucous, vaginal or urethral secretion, cerebrospinal fluid, and transdermal exudate. Bodily fluid also includes experimentally separated fractions of all of the preceding solutions, as well as mixtures containing homogenized solid material, such as feces, tissues, and biopsy samples. The molecule of interest can be, for example, a biomarker (i.e., a molecular indicator associated with a particular pathological or physiological state) present in the bodily fluid that can be assayed to identify risk for, diagnosis of, or progression of a pathological or physiological process in a subject. Examples of biomarkers include proteins, peptides, polypeptides, hormones, prohormones, lipids, glycoproteins, carbohydrates, DNA, RNA, and combinations thereof.

When the analyte is a molecule of interest present in the fluid sample that is introduced into the channel, methods can further involve conjugating the molecule of interest to a particle formed from a first metal to form an analyte complex (e.g., for example by contacting the molecule of interest with a nanoparticle formed from a first metal bound to a recognition element for the molecule of interest, as described in more detail below). Conjugation can occur in the fluid sample prior to introduction into the channel, such that the resulting analyte complex is introduced into the channel. Alternatively, conjugation can occur in situ within the device (e.g., by contacting the molecule of interest with a nanoparticle formed from a first metal bound to a recognition element that is deposited on or within the channel or a fluid inlet fluidly connected thereto).

In other embodiments, the analyte can be a surrogate for the molecule of interest. The surrogate can be an analyte whose concentration in the fluid flowing through the channel is proportional to the concentration of the molecule of interest in the fluid sample, such that by detecting and/or quantifying the surrogate using the electrochemical methods described herein, the molecule of interest can be detected and/or quantified. By way of example, a fixed analyte support (e.g., an aptamer that specifically binds a molecule of interest) can be immobilized on or within the channel or a fluid inlet fluidly connected thereto. A surrogate (e.g., a recognition element for the aptamer such as a polynucleotide probe having a complementary sequence to a portion of the aptamer) can be bound to the fixed analyte support. When the surrogate-fixed analyte support conjugate is contacted with the molecule of interest, the molecule of interest binds to the fixed analyte support, displacing the surrogate. The surrogate then functions as the analyte in the detection methods described above.

The particle formed from the first metal can be any shape (e.g., a sphere, a rod, a quadrilateral, an ellipse, a triangle, a polygon, etc.). In some examples, the shape of the particle formed from the first metal can be selected to facilitate the detection of the analyte. The particle formed from the first metal can be, for example, a nanoparticle formed from a first metal. The particle formed from the first metal can comprise any suitable metal, such as silver, platinum, palladium, copper, nickel, rhodium, technetium, rhenium, antimony, iridium, bismuth, cadmium, cobalt, iron, or combinations thereof. In certain cases, the particle formed from the first metal can comprise a metal selected from the group consisting of silver, copper, nickel, rhodium, technetium, rhenium, antimony, iridium, bismuth, cadmium, cobalt, and combinations thereof. In particular embodiments, the particle formed from the first metal can comprise silver. The particle formed from the first metal can also comprise a suitable compound of the first metal, such as, for example, a halide, and/or chalcogenide of the first metal, such as AgI, AgCl, $Cd_3P_2$, CdS, CdSe, CdTe, $Cu_2S$, $HgI_2$, PbS or ZnS.

Suitable particles of the first metal can be selected in view of a number of factors, including the identity of the second metal, the presence or absence of other species present in the fluid sample flowing through the channel, the nature of the electrochemical techniques employed, the desired stability of the metal particle towards environmental conditions (e.g., stability in air), compatibility with a desired means of conjugation to the analyte, and combinations thereof. For example, in some embodiments, the particle formed from the first metal can be formed from a metal or metal compound that is not present (or is only present at low levels) in the fluid sample flowing through the channel. In some cases, the particle formed from the first metal can be selected such that it can be undergo galvanic exchange with ions of the second metal (e.g., the particle formed from the first metal can be selected such that it has a relatively lower reduction potential compared to the second metal). In some cases, the particle formed from the first metal can be selected such that it is relatively less noble than the second metal.

The analyte can be conjugated to the particle formed from the first metal by any suitable covalent or non-covalent means. In some embodiments, the analyte can be bound to the particle formed from the first metal by a recognition element. For example, the particle formed from the first metal can be bound (via any non-covalent or covalent means) to a recognition element for the analyte, which can be bound to the analyte.

Recognition elements for particular analytes are known in the art. An appropriate recognition element for the formation of an analyte conjugate can be selected in view of a number of considerations including analyte identity, analyte concentration, and the nature of the sample in which the analyte is to be bound. Suitable recognition elements include antibodies, antibody fragments, antibody mimetics (e.g., engineered affinity ligands such as AFFIBODY® affinity ligands), peptides (natural or modified peptides; e.g. a natriuretic peptide), proteins (e.g., recombinant proteins, host proteins, bacterial proteins), polynucleotides (e.g., DNA or RNA, oligonucleotides, aptamers, or DNAzymes), receptors, enzymes, ligands, antigens, organic small molecules (e.g., antigen or enzymatic co-factors), and combinations thereof.

In some embodiments, the recognition element selectively associates with the analyte. The term "selectively associates", as used herein when referring to a recognition element, refers to a binding reaction, which is determinative for the analyte in a heterogeneous population of other similar compounds. Generally, the interaction is dependent upon the presence of a particular structure (e.g., an antigenic determinant or epitope) on the binding partner. By way of example, an antibody or antibody fragment selectively associates to its particular target (e.g., an antibody specifically binds to an antigen) but it does not bind in a significant amount to other proteins present in the sample or to other proteins to which the antibody may come in contact in an organism.

In some embodiments, a recognition element can be a molecule that has an affinity constant ($K_a$) greater than about $10^5$ M$^{-1}$ (e.g., greater than about $10^6$ M$^{-1}$, greater than about $10^7$ M$^{-1}$, greater than about $10^8$ M$^{-1}$, greater than about $10^9$ M$^{-1}$, greater than about $10^{10}$ M$^{-1}$, greater than about $10^{11}$ M$^{-1}$, greater than about $10^{12}$ M$^{-1}$, or more) with that analyte.

In certain embodiments, the recognition element comprises an antibody. The term "antibody" refers to natural or synthetic antibodies that selectively bind a target antigen. The term includes polyclonal and monoclonal antibodies. In addition to intact immunoglobulin molecules, also included in the term "antibodies" are fragments or polymers of those immunoglobulin molecules, and human or humanized versions of immunoglobulin molecules that selectively bind the target antigen. The term encompasses intact and/or full length immunoglobulins of types IgA, IgG (e.g., IgG1, IgG2, IgG3, IgG4), IgE, IgD, IgM, IgY, antigen-binding fragments and/or single chains of complete immunoglobulins (e.g., single chain antibodies, Fab fragments, F(ab')2 fragments, Fd fragments, scFv (single-chain variable), and single-domain antibody (sdAb) fragments), and other proteins that include at least one antigen-binding immunoglobulin variable region, e.g., a protein that comprises an immunoglobulin variable region, e.g., a heavy (H) chain variable region (VH) and optionally a light (L) chain variable region (VL). The light chains of an antibody may be of type kappa or lambda.

An antibody may be polyclonal or monoclonal. A polyclonal antibody contains immunoglobulin molecules that differ in sequence of their complementarity determining regions (CDRs) and, therefore, typically recognize different epitopes of an antigen. Often a polyclonal antibody is derived from multiple different B cell lines each producing an antibody with a different specificity. A polyclonal antibody may be composed largely of several subpopulations of antibodies, each of which is derived from an individual B cell line. A monoclonal antibody is composed of individual immunoglobulin molecules that comprise CDRs with the same sequence, and, therefore, recognize the same epitope (i.e., the antibody is monospecific). Often a monoclonal antibody is derived from a single B cell line or hybridoma. An antibody may be a "humanized" antibody in which for example, a variable domain of rodent origin is fused to a constant domain of human origin or in which some or all of the complementarity-determining region amino acids often along with one or more framework amino acids are "grafted" from a rodent, e.g., murine, antibody to a human antibody, thus retaining the specificity of the rodent antibody.

An appropriate analyte conjugate and localization element can be selected in combination so as to facilitate accumulation of the analyte conjugate in the region of the channel in electrochemical contact with a working electrode. For example, in some embodiments, the analyte conjugate is charged (e.g., the analyte itself is charged, or the analyte is conjugated to a charged moiety such as a charged molecule or charged particle), and the localization element comprises a localization electrode configured to apply an electric field to the region of the channel, so as to increase the concentration of the charged analyte conjugate in the region of the channel in electrochemical contact with the working electrode. In these embodiments, methods of detecting the analyte can comprise flowing fluid comprising the charged analyte conjugated to the particle formed from the first metal along the channel, and applying an electric field via one or more localization electrodes to accumulate the charged analyte conjugated to the particle formed from the first metal in the region of the channel in electrochemical contact with a working electrode.

In some embodiments, the localization element can comprise a physical barrier disposed in the region of the channel in electrochemical contact with the working electrode. The physical barrier can be any suitable material configured to physically entrap the analyte conjugate. For example, the physical barrier can be a porous hydrophilic material (e.g., paper) or a matrix of polymer beads disposed within the fluid flow path formed by the channel that can physically entrap the analyte conjugate. In some embodiments, the analyte conjugate can further include a steric particle (e.g., a microbead) conjugated to the analyte and/or the particle formed from the first metal to increase the hydrodynamic volume of the analyte, thereby facilitating entrapment of the analyte conjugate in the physical barrier. In these embodiments, methods of detecting the analyte can comprise flowing fluid comprising the analyte conjugated to the particle formed from the first metal along the channel to contact the physical barrier such that the analyte accumulates in the region of the channel in electrochemical contact with a working electrode.

In certain embodiments, the localization element can comprise a magnet configured to apply a magnetic field in the region of the channel in electrochemical contact with the working electrode, and the analyte conjugate can comprise a magnetic moiety. For example, the analyte conjugate can comprise an analyte conjugated to a particle formed from a first metal and a magnetic particle.

The magnetic particle can be any magnetic particle that can be conjugated to the analyte and which can provide for localization of the bound analyte under an applied magnetic field. For example, the magnetic particle can be a magnetic microbead. Magnetic microbeads are superparamagnetic, monodisperse, polymer beads that comprise a dispersion of a magnetic material (e.g., gamma $Fe_2O_3$ and $Fe_3O_4$) throughout the polymer bead. The microbeads are coated with a thin polymer shell, which encases the magnetic material and provides a defined surface area for the adsorption or coupling of various molecules. Suitable magnetic microbeads are known in the art, and are commercially available from Life Technologies under the tradename DYNABEADS®.

The analyte can be conjugated to the magnetic particle by any suitable covalent or non-covalent means. In some embodiments, the analyte can be bound to the magnetic particle by a recognition element, as described above. For example, the magnetic particle can be bound (via any non-covalent or covalent means) to a recognition element for the analyte that can be bound to the analyte.

In certain embodiments, the localization element can comprise a magnet configured to apply a magnetic field in the region of the channel in electrochemical contact with the working electrode, and the analyte conjugate can comprise an analyte bound to a first antibody and a second antibody, wherein a particle formed from a first metal is bound to the first antibody and a magnetic particle is bound to the second antibody.

In certain embodiments, the localization element can comprise a magnet configured to apply a magnetic field in the region of the channel in electrochemical contact with the working electrode, and the analyte conjugate can comprise an analyte bound to a first polynucleotide and a second polynucleotide, wherein a particle formed from a first metal is bound to the first polynucleotide and a magnetic particle is bound to the second polynucleotide. In some of these embodiments, the analyte comprises a polynucleotide.

In these embodiments, methods of detecting the analyte can comprise flowing fluid comprising the analyte conjugated to the particle formed from the first metal and the magnetic particle along the channel, and applying the magnetic field to accumulate the analyte conjugated to the particle formed from the first metal and the magnetic particle in the region of the channel.

The methods can further comprise providing ions of a second metal to galvanically exchange with the first metal (e.g., providing a source of the ions of the second metal to the region of the channel). The ions of the second metal can be provided by any suitable means. In some examples, providing a source of the ions of the second metal to the region of the channel comprises providing a compound comprising the second metal. Suitable compounds of the second metal include, for example, an oxide, halide, and/or chalcogenide of the second metal, such as $AuCl_3$, $Ag_2O$, $AgCl$, $AgI$, $Bi_2O_5$, $CuO$, $Cd_3P_2$, $CdS$, $CdSe$, $CdTe$, $Co_2O_3$, $CrO_3$, $Cu_2S$, $HgI_2$, $MnO_2$, $PbS$, $PbO_2$, $SnO_2$, $TiO_2$, $RuO_2$, $ZnO$, $ZnS$ or $ZnO_2$. For example, oxides of the second metal can be dissolved with acid to form ions that may galvanically exchange with the first metal. In some embodiments, oxides of the second metal can galvanically exchange with the first metal. In some embodiments, acid can be electrogenerated at an electrode (for example, by oxidation of water), and that acid can dissolve compounds of the second metal.

In certain examples, the analyte conjugate can be provided (e.g., accumulated) at a working electrode. The working electrode can comprise the second metal (e.g., a layer of the second metal) that can be electrochemically oxidized to provide the ions of the second metal. The second metal can have a higher reduction potential than the first metal (e.g., the second metal is more noble than the first metal). The second metal can comprise any suitable metal, such as gold, silver, copper, platinum, rhodium, palladium, iron, technetium, rhenium, antimony, iridium, nickel, bismuth, cadmium, cobalt, or combinations thereof. In some examples, the second metal can comprise gold, silver, copper, platinum, palladium, iron, nickel, cobalt, or a combination thereof. In some examples, the second metal comprises gold.

The second metal can be selected in view of a number of factors, including the identity of the first metal, the presence or absence of other species present in the fluid sample flowing through the channel, the nature of the electrochemical techniques employed, the desired stability of the metal towards environmental conditions (e.g., stability in air), and combinations thereof. For example, in some embodiments, the second metal can be a metal or metal compound that is not present (or is only present at low levels) in the fluid sample flowing through the channel. In some cases, the second metal can be selected such that it can be undergo galvanic exchange with the first metal (e.g., the second metal can be selected such that is has a higher reduction potential compared to the first metal). In some cases, the second metal can be selected such that it is relatively more noble than the first metal.

As described above, galvanically exchanging the first metal with ions of the second metal can form a product of the galvanic exchange, which can be detected. In the galvanic exchange reactions, the particle formed from the first metal reacts with the ions of the second metal, where the reaction is a redox reaction that favors reduction and deposition of the second metal (through replacement) and oxidation and dissolution of the first metal. A reduction potential is the measure (in voltage) of the tendency for a chemical species to be reduced (a higher reduction potential means the metal is easier to reduce). In order for galvanic exchange to take place between the first and second metal, the ions of the second metal must have a higher reduction potential than the first metal. Both the first metal and second metal can be in a complexed state, which can shift the reduction potential in a favorable or unfavorable direction. The magnitude of the difference between the reduction potential of the first metal and the reduction potential of the second metal can indicate the likelihood or spontaneity of the galvanic exchange reaction to proceed. For example, gold ions will spontaneously exchange with solid silver (Reaction 1) in bulk solution based on the standard reduction potential ($E^0$) of gold (Reaction 2) being more positive than that of silver (Reaction 3). Similarly, any two metals whose reduction potentials differ ($\Delta E$) by 0.10 V or more (e.g., 0.15 V or more, 0.2 V or more, 0.25 V or more, 0.3 V or more, 0.35 V or more, 0.4 V or more, 0.45 V or more, or 0.5 V or more) are expected, from a thermodynamic point of view, to spontaneously undergo galvanic exchange to completion.

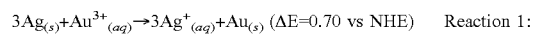

Reaction 1: $3Ag_{(s)} + Au^{3+}_{(aq)} \rightarrow 3Ag^+_{(aq)} + Au_{(s)}$ ($\Delta E = 0.70$ vs NHE)

Reaction 2: $Au^{3+}_{(aq)} + 3e^- \rightarrow Au_{(s)}$ ($E^0 = 1.50$ vs NHE)

Reaction 3: $Ag^+_{(aq)} + e^- \rightarrow Ag_{(s)}$ ($E^0 = 0.80$ vs NHE)

In some examples, the product of the galvanic exchange can comprise a plurality of particles formed from the second metal. Forming the plurality of particles from the second metal can, in some examples, result in a color change. Detecting the product of the galvanic exchange can comprise spectroscopically detecting the plurality of particles formed from the second metal, spectroscopically detecting the color change, observing the color change (e.g., visually), or a combination thereof.

For example, if the second metal comprises gold the galvanic exchange can form a plurality of gold nanoparticles. Gold nanoparticles can have a surface plasmon resonant energy in the visible region of the electromagnetic spectrum (e.g., from the "green" wavelength to the NIR). The surface plasmon resonance of the gold nanoparticles can be detected spectroscopically (e.g., using a UV-Vis spectrometer). Colloidal solutions of gold nanoparticles can also exhibit brilliant, enduring colors, such that in some examples the formation of gold nanoparticles can be detected visually by observing a color change as the gold nanoparticles are formed. Colloidal solutions of gold nanoparticles can be stable, such that the color exhibited by the solution can persist for extended periods of time (e.g., over a century in some cases).

In some examples, the analyte conjugated to the particle formed from the first metal can be provided at a working electrode, and the product of the galvanic exchange can comprise a layer of the first metal formed at the working electrode. In these embodiments, detecting the product of the galvanic exchange can comprise electrochemically detecting the first metal. For example, the potential applied at the working electrode can be then varied to oxidize the layer of first metal at the working electrode to ions of the first metal. Various techniques of electrochemical analysis may be used to assay the layer of the first metal formed at the working electrode. For example, the first metal can be detected using anodic stripping voltammetry with a potential scan which may be linear, cyclic, square-wave, normal pulse or differential pulse, or with a superimposed sinusoidal voltage, or else anodic stripping chronopotentiometry. However, other techniques may be used, such as ion exchange voltammetry, adsorptive cathodic stripping voltammetry (or polarography) with a scan which may be linear, cyclic, square-wave, normal pulse or differential pulse, or with a superimposed sinusoidal voltage, or else chronoamperometry, chronocoulometry or linear, cyclic, square-wave, normal pulse or differential pulse voltammetry (or polarography) or voltammetry (or polarography) with a superimposed sinusoidal voltage. These techniques require a possibly two-electrode or even three-electrode assembly, e.g., an assembly comprising the working electrode, a reference electrode, and a counter electrode.

In certain cases, for example, the second metal can be gold, which in its bulk metal form is stable indefinitely, and the first metal can be silver (e.g., particles formed from silver, such as silver nanoparticles). In these cases, the potential applied to the gold working electrode (e.g., a solid gold electrode, or an electrode with a layer of gold deposited thereon) can be varied to oxidize the Au to $Au^{3+}$. The $Au^{3+}$ galvanically exchanges with the silver particles localized at the working electrode, which results in $Au^0$ and oxidized $Ag^+$. One of the benefits of using galvanic exchange to oxidize silver is that $Au^{3+}$ is a mild oxidant that is stable indefinitely (in the form of $Au^0$ at the working electrode) and will primarily oxidize the silver particles in a controlled manner near the electrode surface. In contrast, chemical oxidants usually have a short shelf life, are difficult to prepare for manufacturing and storage purposes, and may detrimentally exert their non-specific oxidative effects on the other reagents and materials of the device. Consequently, the galvanic exchange can provide a more selective, simple, and stable way to oxidize the particles of the first metal than, for example, contact with a chemical oxidant.

A variety of potential assays (e.g., sandwich-type assays, competitive binding assays, etc.) can be envisioned that employ the electrochemical detection methods described above for analyte detection and/or quantification. The precise design of such assays will vary based on, for example, the nature of the analyte and the localization element used.

The methods described herein can be practiced in any suitable device. In some examples, the methods are performed in a well of a microtiter plate. In some examples, the methods are performed in an electrochemical cell.

Devices

Also provided are devices for the detection of analytes. The devices can be used to practice the detection methods described above. In some examples, the devices can comprise a channel defining a path for fluid flow from a fluid inlet to a fluid outlet, a working electrode positioned in electrochemical contact with a region of the channel, and a localization element configured to accumulate the analyte conjugated to the particle formed from the first metal (i.e., the analyte conjugate) in the region of the channel in electrochemical contact with the working electrode. As described above, the localization element can be any feature that is configured to increase the concentration of the analyte conjugate in the region of the channel in electrochemical contact with the working electrode in the presence of fluid flow through the channel. For example, the localization element can be a physical barrier disposed in the region of the channel in electrochemical contact with the working electrode (e.g., a material configured to physically entrap the analyte conjugate), one or more localization electrodes configured to apply an electric field to the region of the channel in electrochemical contact with the working electrode (e.g., configured to electrophoretically localize the analyte conjugate), a magnet configured to apply a magnetic field in the region of the channel in electrochemical contact with the working electrode, or a combination thereof. Devices can further include a counter electrode, a reference electrode, or combinations thereof in electrochemical contact with the channel.

The devices can further comprise an engageable platform that can be translocated from a retracted position to a deployed position. When the engageable platform is in the retracted position, the engageable platform is fluidly independent from the channel (e.g., engageable platform is positioned in a region of the device such that the engageable platform is not in fluid contact with the channel). When the engageable platform is in the deployed position, the engageable platform is in fluid contact with the region of the channel in electrochemical contact with the electrode (e.g., engageable platform is positioned in fluid contact with the region of the channel in electrochemical contact with the electrode).

The engageable platform can be provided, for example, as a portion of a translocatable layer of a multilayer microfluidic device, as described in more detail below. Alternatively, the engageable platform can be provided independently from one or more layers that combine to form a microfluidic device (e.g., as part of a translocatable region within a stationary layer of a multilayer microfluidic device). The engageable platform can be formed from a porous, hydrophilic material, such as paper. In some examples, a source of ions of a second metal can be disposed on the engageable platform (e.g., adsorbed or absorbed so the engageable platform). The source of the ions of the second metal can be any suitable source of the ions of the second as described above (e.g., a compound comprising the second metal). Such engageable platforms have been described, for example, in PCT/US2014/071389, which is incorporated herein by reference.

The devices described herein can be fabricated from any suitable material or combination of materials. In some embodiments, the devices are paper-based microfluidic devices (devices fabricated from one or more layers of paper). Paper-based microfluidic devices include a channel (i.e., a path such as a conduit, through which one or more fluids can flow) formed within a layer of a porous, cellulosic substrate. The channel can be a void space through which a fluid can flow, a porous hydrophilic substrate such as paper through which fluid flows by wicking (i.e., a filled channel), or a combination thereof. In some examples, the channel for paper-based microfluidic devices can be a "hollow channel," for example as described in Renault C et al. "Hollow-channel Paper Analytical Devices" *Anal. Chem.* 2013, 85, 7976-7979 (DOI: 10.1021/ac401786h). A hollow channel can, for example, comprise a void space through which fluid can flow. In certain examples, the hollow channel can further comprise at least one hydrophilic surface in contact with the fluid that can promote capillary flow of aqueous solutions. In certain examples, wherein the hollow channel does not further comprise a hydrophilic surface, high pressures can be used to induce flow in the microfluidic channels. In some examples, the at least one hydrophilic surface can comprise a hemichannel. Hemichannels are described, for example, in Renault C et al. "Three-Dimensional Wax Patterning of Paper Fluidic Devices" *Langmuir* 2014, 30, 7030-7036 (DOI: 10.1021/1a501212b) and Renault C et al. "Electrochemistry in hollow-channel paper analytical devices" *J. Am. Chem. Soc.* 2014, 136, 4616-4623.

The dimensions of the channel within the layer of porous, cellulosic substrate are defined by a hydrophobic boundary that substantially permeates the thickness of the porous, cellulosic substrate, so as to form a boundary for fluid flow from the channel to a region on the porous, cellulosic substrate outside of the channel, thereby directing fluid flow along the channel.

The channel can be patterned within a layer of a porous, cellulosic substrate using any suitable method known in the art. For example, the channel can be patterned by wax printing. In these methods, an inkjet printer is used to pattern a wax material on the porous, cellulosic substrate. Many types of wax-based solid ink are commercially available and are useful in such methods as the ink provides a visual indication of the location of the channels. However, it should be understood, that the wax material used to form the channels does not require an ink to be functional. Examples of wax materials that may be used include polyethylene waxes, hydrocarbon amide waxes or ester waxes. Once the wax is patterned, the porous, cellulosic substrate is heated (e.g., by placing the substrate on a hot plate with the wax side up at a temperature of 130° C.) and cooled to room temperature. This allows the wax material to substantially permeate the thickness of the porous, cellulosic substrate, so as to form a hydrophobic boundary that defines the dimensions of the channel. At this point, the resulting channel is a filled channel, as the channel defined by the hydrophobic boundary includes a porous hydrophilic substrate (the porous, cellulosic substrate) through which fluid can flow by wicking. In some examples, wax can be patterned to form a hemichannel. For example, the hemichannel can be formed by patterning the wax such that in certain locations the wax partially permeates through the thickness of the porous, cellulosic substrate and in certain other locations the wax substantially permeates through the thickness of the porous, cellulosic substrate. For example, the hemichannel can be fabricated by adjusting the amount of wax printed on the porous, cellulosic substrate such that a hemicylinder of hydrophilic substrate is surrounded by a wax barrier. If desired for device design, a hollow channel can be formed by removing at least a portion of the porous, cellulosic substrate within the hydrophobic boundary, thereby forming a void space.

In some examples, a hollow channel comprises a hemichannel. A three-dimensional perspective of an example of a hollow channel is shown in FIG. 1. For example, a paper device having both filled channels and hemichannels may be fabricated, and then the cellulose can be removed from within the filled channel to leave a void space. After the device is folded into the desired configuration, at least one hemichannel can cap the void space and provide a hydrophilic surface along which an aqueous solution can spontaneously wick. A single hydrophilic wall in an otherwise hydrophobic channel (void space) can, in some examples, be sufficient for capillary filling at low pressures (0.01 to 20 kPa). In certain examples, wherein all four walls of a microfluidic void space are hydrophobic, capillary forces alone may not move the fluid and comparatively high pressures (exceeding 20 kPa) can be required to drive the fluids.

In some embodiments, the porous, cellulosic substrate used to form the paper-based microfluidic device is flexible. For certain applications, it is preferable that the cellulosic substrate can be folded, creased, or otherwise mechanically shaped to impart structure and function to the paper-based device formed from the cellulosic substrate. Examples of suitable porous, cellulosic substrates for the fabrication of paper-based microfluidic devices include cellulose; derivatives of cellulose such as nitrocellulose or cellulose acetate; paper (e.g., filter paper, chromatography paper); woven cellulosic materials; and non-woven cellulosic materials.

In some embodiments, the porous, cellulosic substrate is paper. Paper is inexpensive, widely available, readily patterned, thin, lightweight, and can be disposed of with minimal environmental impact. Furthermore, a variety of grades of paper are available, permitting the selection of a paper substrate with the weight (i.e., grammage), thickness and/or rigidity and surface characteristics (i.e., porosity, hydrophobicity, and/or roughness), desired for the fabrication of a particular paper-based device. Suitable papers include, but are not limited to, chromatography paper, card stock, filter paper, vellum paper, printing paper, wrapping paper, ledger paper, bank paper, bond paper, blotting paper, drawing paper, fish paper, tissue paper, paper towel, wax paper, and photography paper.

In certain embodiments, the localization element can comprise a magnet configured to apply a magnetic field in the region of the channel in electrochemical contact with the working electrode. In these embodiments, the devices can comprise a channel defining a path for fluid flow from a fluid inlet to a fluid outlet, an electrode positioned in electrochemical contact with a region of the channel, and a magnet configured to apply a magnetic field to the region of the channel positioned in electrochemical contact with the electrode.

Figure 2:
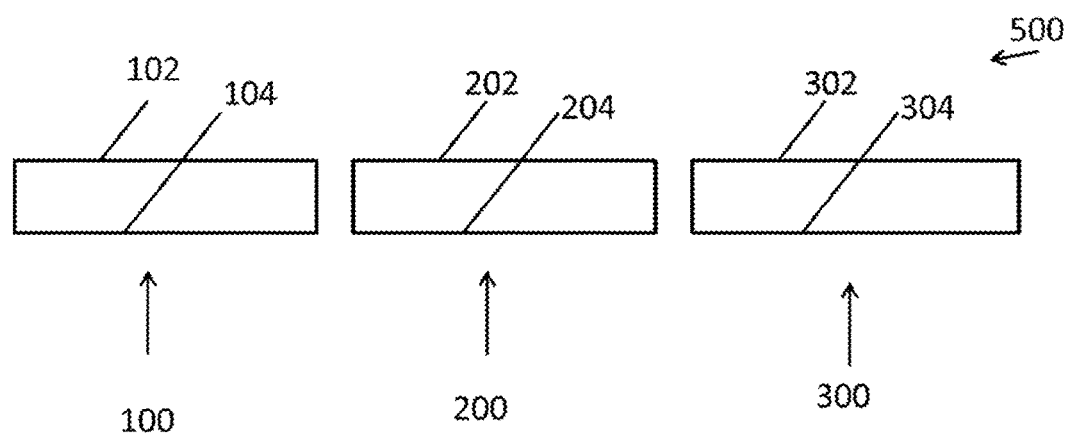
FIG. 2 is a schematic side view of the three layers of a device for the detection of analytes as viewed along the axis of fluid flow.
Figure 3:
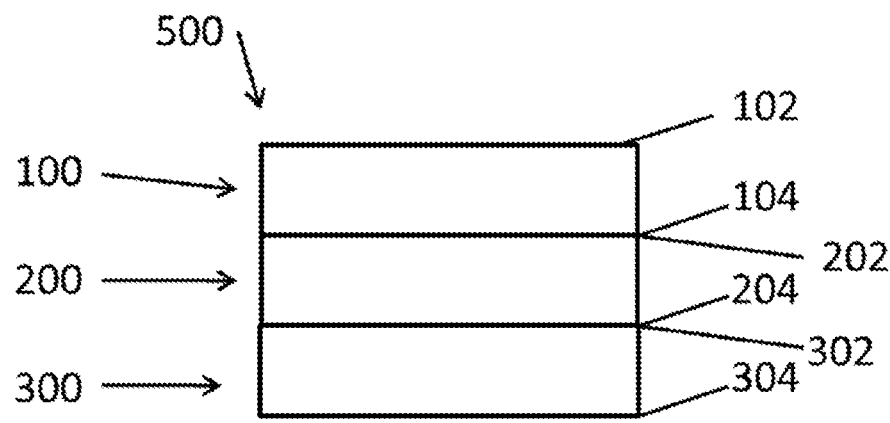
FIG. 3 displays a schematic side view of the assembled three layer device for the detection of analytes as viewed along the axis of fluid flow.
Figure 4:
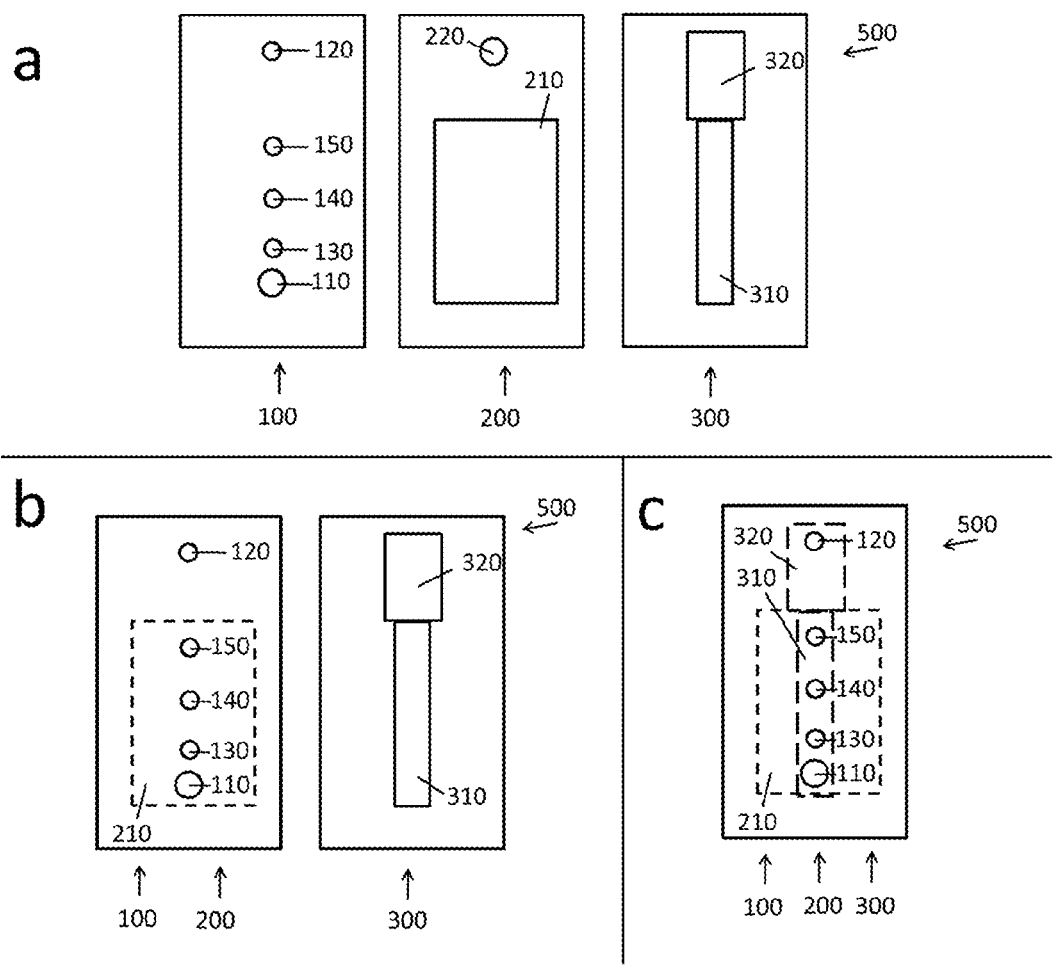
FIG. 4 displays a schematic top view of the three layers of the device for the detection of analytes (panel a), the device with the first layer aligned with the second layer (panel b), and the device with all three layers aligned (panel c).

An example device employing a magnetic localization element is illustrated in FIGS. 2-4. Referring now to FIG. 2, the device (500) includes a first layer (100) having a top surface (102) and a bottom surface (104), a second layer (200) having a top surface (202) and a bottom surface (204), and a third layer (300) having a top surface (302) and a bottom surface (304). Referring now to FIG. 3, when the device (500) is assembled, the bottom surface of the first layer (104) is in contact with the top surface of the second layer (202), and the bottom surface of the second layer (204) is in contact with the top surface of the third layer (302).

Referring now to FIG. 4, panel a, the first layer (100) includes a fluid inlet (110) defining a path for fluid flow from the top surface of the first layer (102) to the bottom surface of the first layer (104), a fluid outlet (120) defining a path for fluid flow from the bottom surface of the first layer (104) to the top surface of the first layer (102), and a working electrode (130) disposed on the bottom surface of the first layer (104). The first layer (100) can also include a reference electrode (140) disposed on the bottom surface of the first layer (104) and a counter electrode (150) disposed on the bottom surface of the first layer (104). The second layer (200) includes a hydrophobic boundary defining a channel (210) for fluid flow within the second layer, and a port (220) defining a path for fluid flow from the bottom surface of the second layer (204) to the top surface of the second layer (202). The third layer (300) comprises a channel (310) defining a path for fluid flow within the third layer formed from a porous hydrophilic material, and a sink (320) fluidly connected to the channel (310) and formed from a porous hydrophilic material.

The device is assembled by aligning the three layers as shown in FIG. 4, panel b and c. Referring now to FIG. 4, panel b, which illustrates the first layer (100) aligned with the second layer (200), the first layer (100) is aligned with the second layer (200) such that the working electrode (130), reference electrode (140), and counter electrode (150) are in electrochemical contact with a region of the channel (210) for fluid flow within the second layer, the fluid inlet (110) is fluidly connected to the channel (210) for fluid flow within the second layer, and the fluid outlet (120) is fluidly connected to the port (220).

FIG. 4, panel b, illustrates a top view of the assembled device (500) with the first layer (100) aligned with the second layer (200) and the third layer (300). The first layer (100), the second layer (200), and the third layer (300) are aligned such that the fluid inlet (110), working electrode (130), reference electrode (140), counter electrode (150), and the channel (210) for fluid flow within the second layer are all aligned over the channel (310) for fluid flow within the third layer. In addition, the fluid outlet (120) is fluidly connected to the port (220) and the sink (320). As such, the first layer (100), the second layer (200), and the third layer (300) are aligned so as to form a continuous path for fluid flow from the fluid inlet (110), to the channel (210) for fluid flow within the second layer, to the channel (310) for fluid flow within the third layer, to the sink (320), to the port (220), to the fluid outlet (120).

Figure 5:
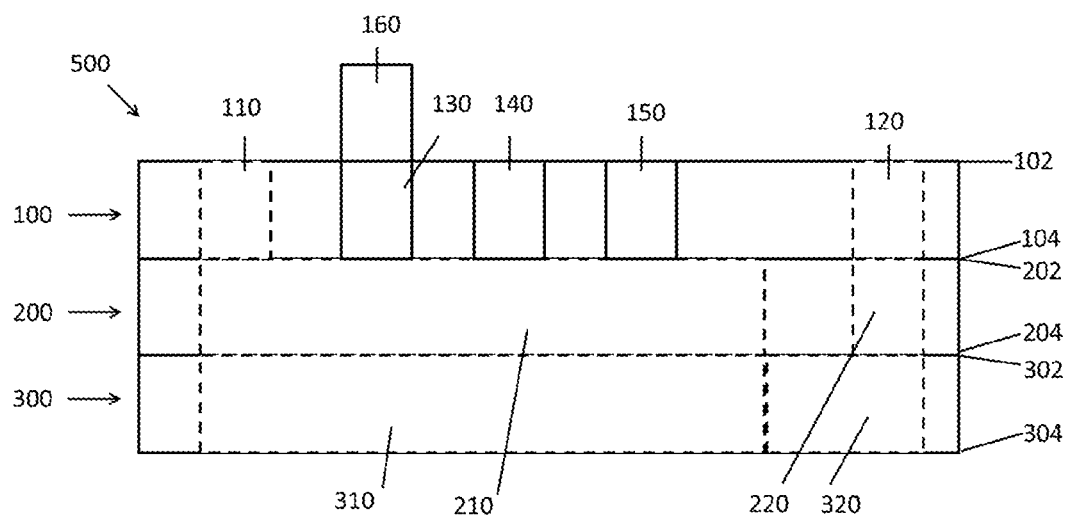
FIG. 5 displays a cutaway side view of the device for the detection of analytes with all three layers aligned as viewed perpendicular to the axis of fluid flow.

Referring now to FIG. 5, the device (500) can further comprise a magnet (160). The magnet (160) is aligned with the working electrode (130) so as to apply a magnetic field within the region of the channel (210) in the second layer in electrochemical contact with the working electrode (130).

Figure 6:
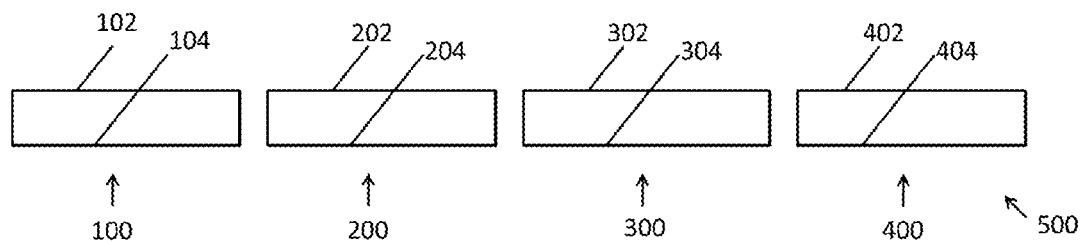
FIG. 6 displays a schematic side view of the four layers of a device for the detection of analytes as viewed along the axis for fluid flow.
Figure 7:
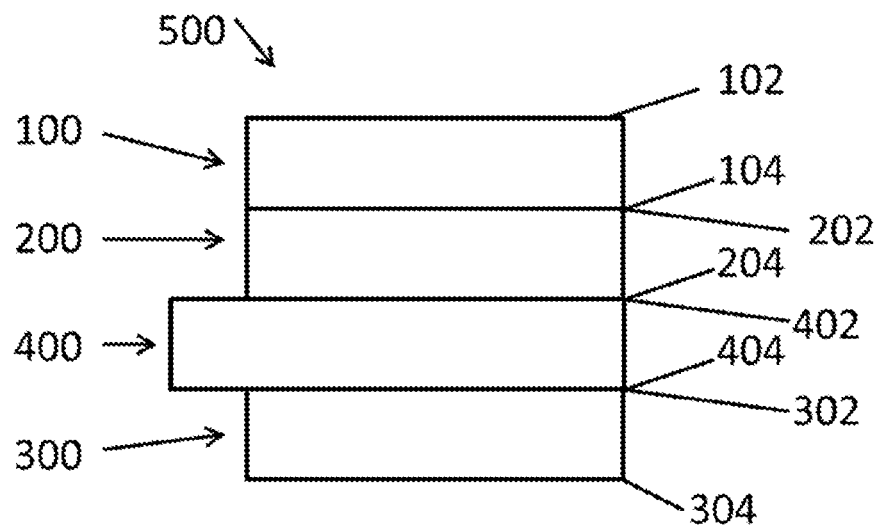
FIG. 7 displays a schematic side view of the assembled four layer device for the detection of analytes as viewed along the axis of fluid flow.

An example device employing a magnetic localization element and an engageable platform is illustrated in FIGS. 6-13. Referring now to FIG. 6, the device (500) includes a first layer (100) having a top surface (102) and a bottom surface (104), a second layer (200) having a top surface (202) and a bottom surface (204), a third layer (300) having a top surface (302) and a bottom surface (304), and an engageable layer (400) having a top surface (402) and a bottom surface (404). Referring now to FIG. 7, when the device (500) is assembled, the bottom surface of the first layer (104) is in contact with the top surface of the second layer (202), the bottom surface of the second layer (204) is in contact with the top surface of the engageable layer (402), and the bottom surface of the engageable layer (404) is in contact with the top surface of the third layer (304).

Figure 8:
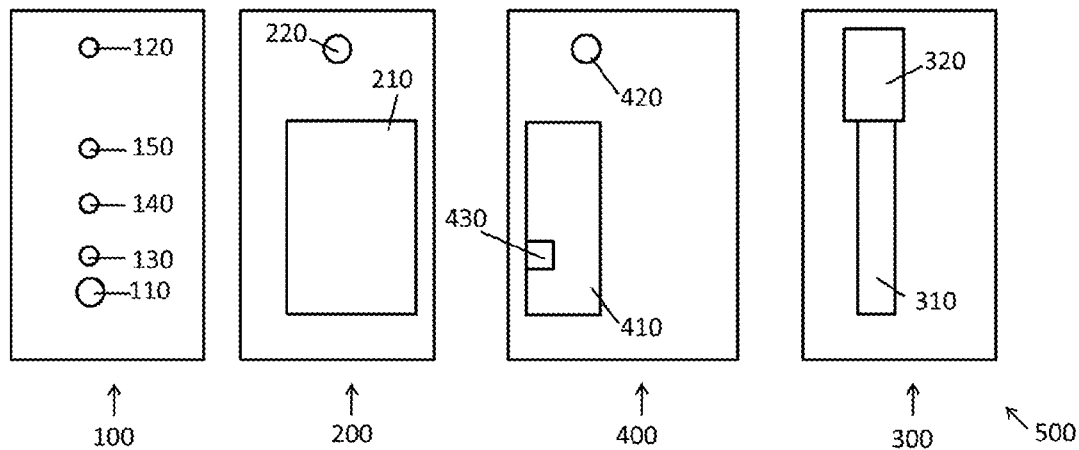
FIG. 8 displays a schematic top view of the four layers of the device for the detection of analytes.

Referring now to FIG. 8, the first layer (100) includes a fluid inlet (110) defining a path for fluid flow from the top surface of the first layer (102) to the bottom surface of the first layer (104), a fluid outlet (120) defining a path for fluid flow from the bottom surface of the first layer (104) to the top surface of the first layer (102), and a working electrode (130) disposed on the bottom surface of the first layer (104). The first layer (100) can also include a reference electrode (140) disposed on the bottom surface of the first layer (104) and a counter electrode (150) disposed on the bottom surface of the first layer (104). The second layer (200) includes a hydrophobic boundary defining a channel (210) for fluid flow within the second layer, and a port (220) defining a path for fluid flow from the bottom surface of the second layer (204) to the top surface of the second layer (202). The engageable layer (400) includes a hydrophobic boundary defining a channel (410) for fluid flow within the engageable layer, a port (420) defining a path for fluid flow from the bottom surface of the engageable layer (404) to the top surface of the engageable layer (402), and an engageable platform (430) disposed within the engageable layer. In some embodiments, the engageable platform (430) comprises a source of the ions of the second metal, as described above. The third layer (300) comprises a channel (310) defining a path for fluid flow within the third layer formed from a porous hydrophilic material, and a sink (320) fluidly connected to the channel (320) and formed from a porous hydrophilic material.

Figure 9:
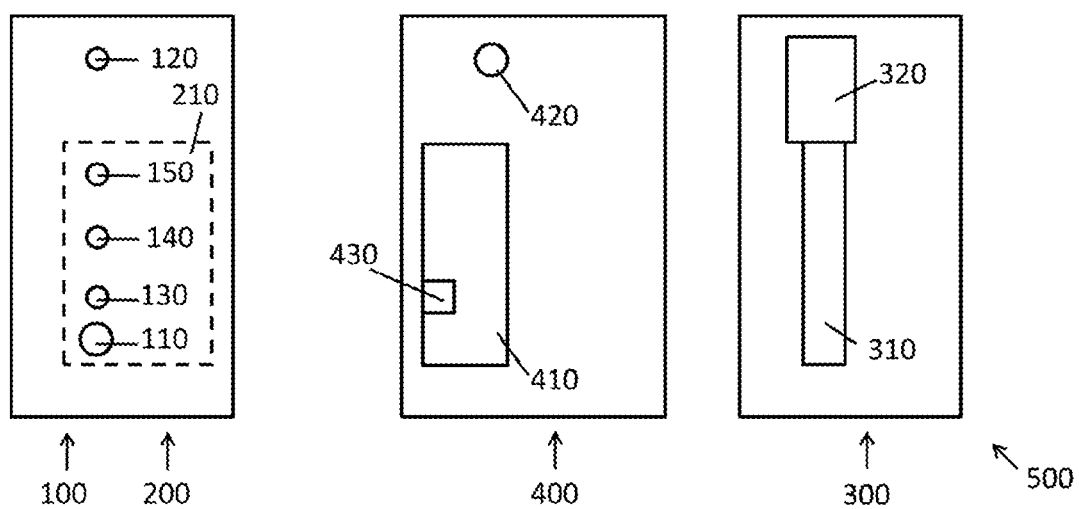
FIG. 9 displays a schematic top view of the device for the detection of analytes, with the first layer aligned with the second layer.

The device is assembled by aligning the four layers as shown in FIG. 7. Referring now to FIG. 9, which illustrates the first layer (100) aligned with the second layer (200), the first layer (100) is aligned with the second layer (200) such that the working electrode (130), reference electrode (140), and counter electrode (150) are in electrochemical contact with a region of the channel (210) for fluid flow within the second layer, the fluid inlet (110) is fluidly connected to the channel (210) for fluid flow within the second layer, and the fluid outlet (120) is fluidly connected to the port (220) within the second layer.

Figure 10:
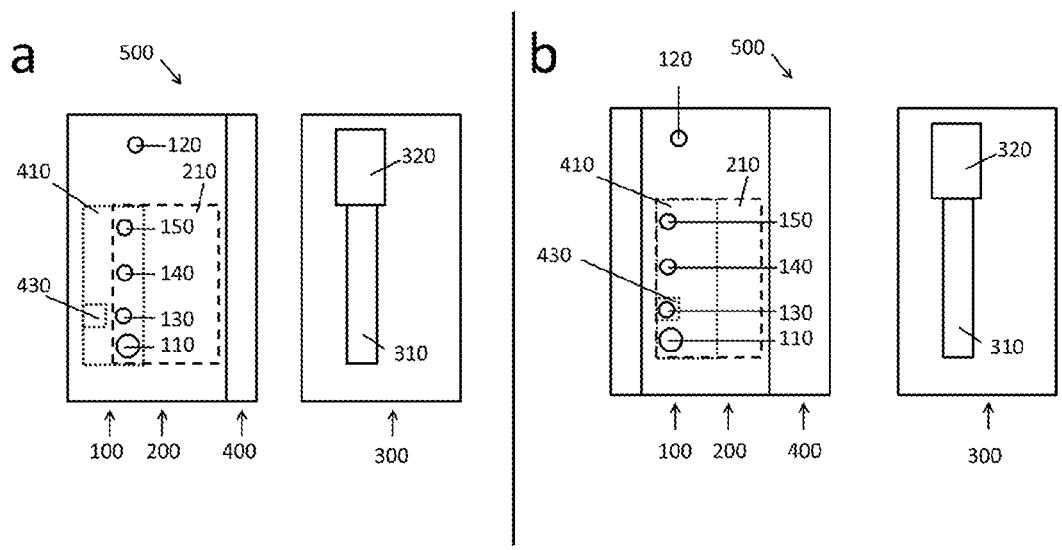
FIG. 10 displays a schematic top view of the device for the detection of analytes, with the first layer aligned with the second layer and the engageable layer in position 1 (panel a) and position 2 (panel b).

FIG. 10 illustrates the first layer (100) aligned with the second layer (200) and the engageable layer (400) in two different positions. In position 1 (the retracted position), shown in FIG. 10, panel a, the first layer (100), the second layer (200), and the engageable layer (400) are aligned such that the fluid inlet (110), working electrode (130), reference electrode (140), counter electrode (150), and the channel (210) for fluid flow within the second layer are all aligned over the channel (410) for fluid flow within the engageable layer. In addition, the engageable platform (430) is fluidly independent from (i.e., not in fluid contact with) the channel (210) for fluid flow within the second layer. In position 2 (the deployed position), shown in FIG. 10, panel b, the first layer (100), the second layer (200), and the engageable layer (400) are aligned such that the fluid inlet (110), working electrode (130), reference electrode (140), counter electrode (150), and the channel (210) for fluid flow within the second layer remain aligned over the channel (410) for fluid flow within the engageable layer. However, the engageable platform (430) is now positioned in fluid contact with the channel (210) for fluid flow within the second layer and aligned with the working electrode (130). The alignment of the layers of the device can be transitioned from position 1 to position to by translocation of the engageable layer (400) relative to the first layer (100) and the second layer (200).

Figure 11:
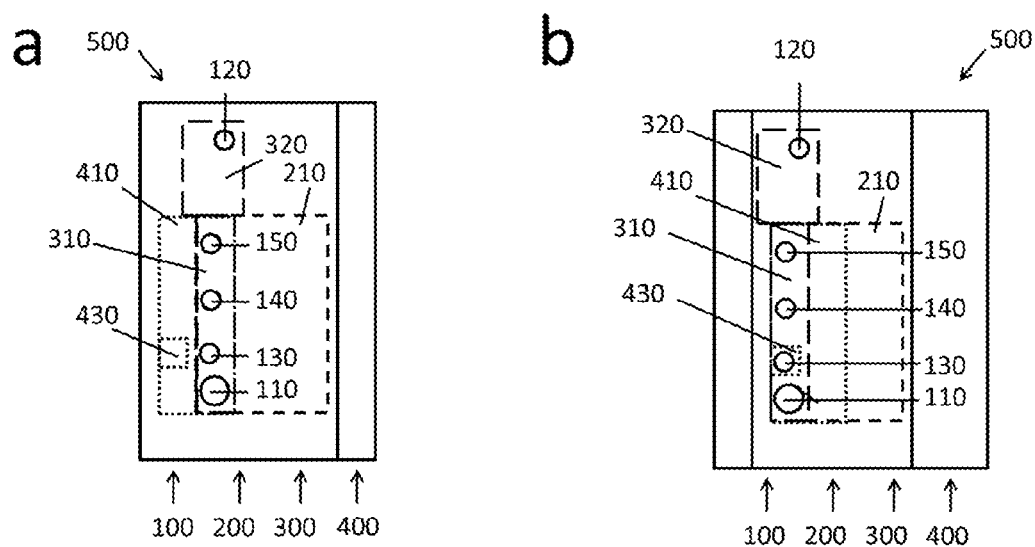
FIG. 11 displays a schematic top view of the device for the detection of analytes, with all four layers aligned position 1 (panel a) and position 2 (panel b).

FIG. 11 illustrates a top view of the assembled device (500) with the first layer (100) aligned with the second layer (200), the engageable layer (400), and the third layer (300) in two different positions. In position 1 (the retracted position), shown in FIG. 11, panel a, the first layer (100), the second layer (200), and the engageable layer (400) are aligned such that the fluid inlet (110), working electrode (130), reference electrode (140), counter electrode (150), and the channel (210) for fluid flow within the second layer are all aligned over the channel (410) for fluid flow within the engageable layer. The third layer (300) is aligned such that the channel (310) is aligned beneath the fluid inlet (110), working electrode (130), reference electrode (140), counter electrode (150), and the channel (210) for fluid flow within the second layer, and such that the channel (310) is in fluid contact with the channel (410) for fluid flow within the engageable layer. In position 1, the first layer (100), the second layer (200), the engageable layer (400), and the third layer (300) are aligned so as to form a continuous path for fluid flow from the fluid inlet (110), to the channel (210) for fluid flow within the second layer, to the channel (410) for fluid flow within the engageable layer, to channel 310, to sink 320, to port 420, port 220, to the fluid outlet (120). The engageable platform (430) is fluidly independent from (i.e., not in fluid contact with) the channel (210) for fluid flow within the second layer. In position 2 (the deployed position), shown in FIG. 11, panel b, the first layer (100), the second layer (200), and the engageable layer (300) are aligned such that the fluid inlet (110), working electrode (130), reference electrode (140), counter electrode (150), and the channel (210) for fluid flow within the second layer remain aligned over the channel (410) for fluid flow within the engageable layer. The third layer (300) remains aligned such that the channel (310) is aligned beneath the fluid inlet (110), working electrode (130), reference electrode (140), counter electrode (150), and the channel (210) for fluid flow within the second layer, and such that the channel (310) is in fluid contact with the channel (410) for fluid flow within the engageable layer. However, the engageable platform (430) is now positioned in fluid contact with the channel (210) for fluid flow within the second layer and aligned with the working electrode (130). The alignment of the layers of the device can be transitioned from position 1 to position to by translocation of the engageable layer (400) relative to the first layer (100), the second layer (200), and the third layer (300).

Figure 12:
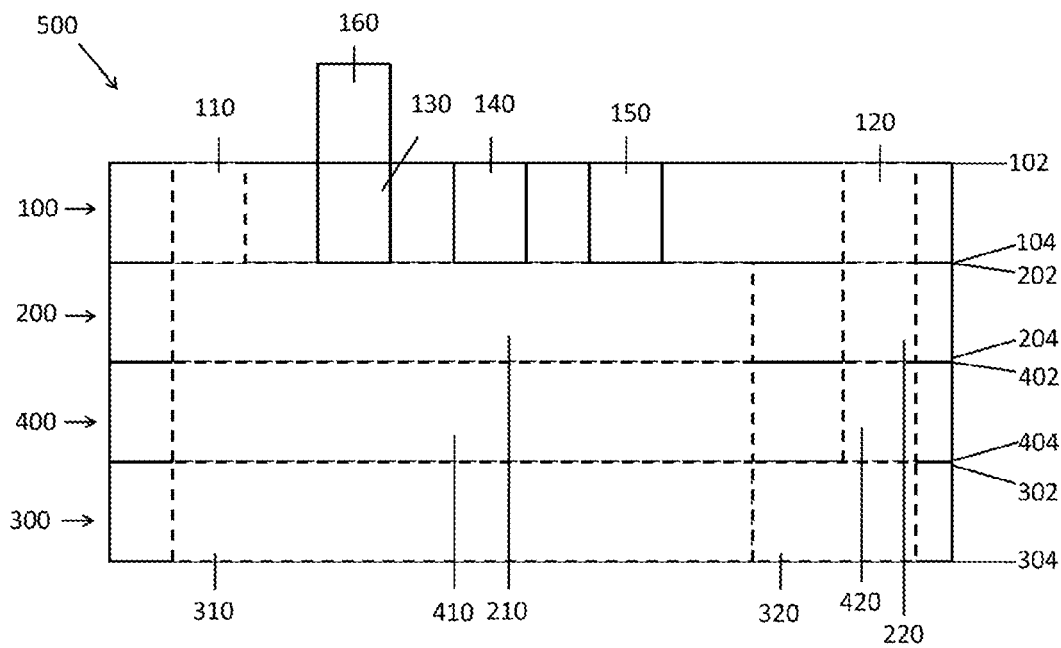
FIG. 12 displays a cutaway side view of the device for the detection of analytes with all four layers aligned in position 1 as viewed perpendicular to the axis of fluid flow.
Figure 13:
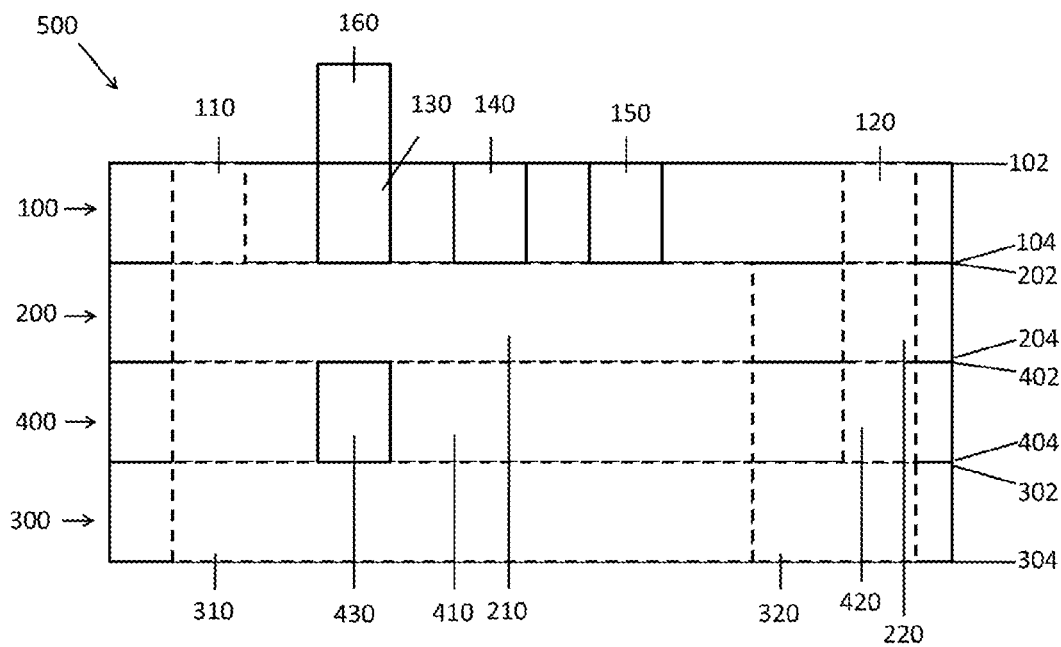
FIG. 13 displays a cutaway side view of the device for the detection of analytes with all four layers aligned in position 2 as viewed perpendicular to the axis of fluid flow.

Referring now to FIG. 12 and FIG. 13, the device (500) can further comprise a magnet (160). The magnet (160) is aligned with the working electrode (130) so as to apply a magnetic field within the region of the channel (210) in the second layer in electrochemical contact with the working electrode (130).

If desired, a reagent for the detection of a molecule of interest can be deposited at the fluid inlet. Optionally, an indicator can be disposed on the sink, the port in the second layer, or combinations thereof. The indicator can be a dye that is transported to the fluid outlet by the fluid flowing through the device, thereby indicating completion of an assay. In certain embodiments, the first layer, the second layer, and the third layer are fabricated from a single (integral) piece of paper that is folded to form the device. Optionally, the fluid outlet can comprise a fluid sink (e.g., a reservoir that can accommodate fluid flow from a channel, until it fills, then flow stops), such that all fluid processed by the device is retained within the device. Similar devices can be fabricated from fewer than three layers (e.g., two layers) or more than two layers (e.g., four layers or five layers).

If desired, the devices described herein can be affixed to or secured within a polymer, metal, glass, wood, or paper support structure to facilitate handling and use of the device. In some embodiments, the devices described herein are affixed to or secured within an inert, non-absorbent polymer such as a polyether block amide (e.g., PEBAX®, commercially available from Arkema, Colombes, France), a polyacrylate, a polymethacrylate (e.g., poly(methyl methacrylate)), a polyimide, polyurethane, polyamide (e.g., Nylon 6,6), polyvinylchloride, polyester, (HYTREL®, commercially available from DuPont, Wilmington, Del.), polyethylene (PE), polyether ether ketone (PEEK), fluoropolymers such as polytetrafluoroethylene (PTFE), perfluoroalkoxy, fluorinated ethylene propylene, or a blend or copolymer thereof. Silastic materials and silicon based polymers can also be used.

The devices described herein can be coupled to a power supply and optionally to one or more additional suitable features including, but not limited to, a voltmeter, an ammeter, a multimeter, an ohmmeter, a signal generator, a pulse generator, an oscilloscope, a frequency counter, a potentiostat, or a capacitance meter. The devices described herein can also be coupled to a computing device that performs arithmetic and logic operations necessary to process the electrochemical signals produced by the device (e.g., to determine analyte concentration, etc.).

Figure 14:
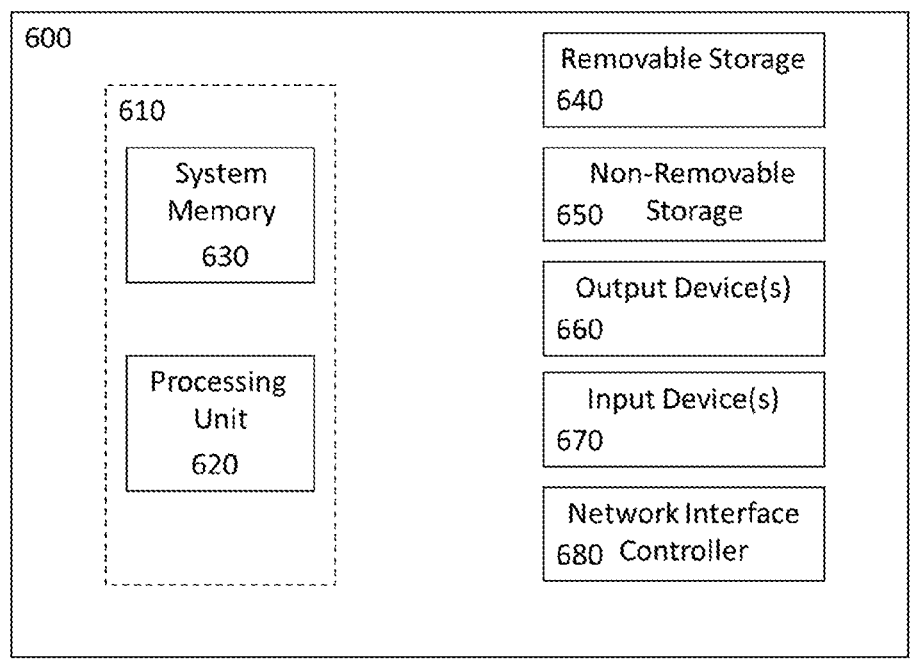
FIG. 14 is a schematic of an exemplary computing device.

FIG. 14 illustrates a suitable computing device upon which the methods disclosed herein may be implemented. The computing device 600 can include a bus or other communication mechanism for communicating information among various components of the computing device 600. In its most basic configuration, a computing device 600 typically includes at least one processing unit 620 (a processor) and system memory 630. As used herein, processor refers to a physical hardware device that executes encoded instructions for performing functions on inputs and creating outputs. Depending on the exact configuration and type of computing device 600, the system memory 630 may be volatile (such as random access memory (RAM)), non-volatile (such as read-only memory (ROM), flash memory, etc.), or some combination of the two. This most basic configuration is illustrated in FIG. 14 by a dashed line 610. The processing unit 620 may be a standard programmable processor that performs arithmetic and logic operations necessary for operation of the computing device 600.

The computing device 600 can have additional features/functionality. For example, the computing device 600 may include additional storage such as removable storage 640 and non-removable storage 650 including, but not limited to, magnetic or optical disks or tapes. The computing device 600 can also contain network connection(s) 680 that allow the device to communicate with other devices. The computing device 600 can also have input device(s) 670 such as a keyboard, mouse, touch screen, antenna or other systems configured to communicate with the camera in the system described above, etc. Output device(s) 660 such as a display, speakers, printer, etc. may also be included. The additional devices can be connected to the bus in order to facilitate communication of data among the components of the computing device 600.

The processing unit 620 can be configured to execute program code encoded in tangible, computer-readable media. Computer-readable media refers to any media that is capable of providing data that causes the computing device 600 (i.e., a machine) to operate in a particular fashion. Various computer-readable media can be utilized to provide instructions to the processing unit 620 for execution. Common forms of computer-readable media include, for example, magnetic media, optical media, physical media, memory chips or cartridges, a carrier wave, or any other medium from which a computer can read. Example computer-readable media can include, but is not limited to, volatile media, non-volatile media and transmission media. Volatile and non-volatile media can be implemented in any method or technology for storage of information such as computer readable instructions, data structures, program modules or other data and common forms are discussed in detail below. Transmission media can include coaxial cables, copper wires and/or fiber optic cables, as well as acoustic or light waves, such as those generated during radio-wave and infra-red data communication. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

For example, the processing unit 620 can execute program code stored in the system memory 630. For example, the bus can carry data to the system memory 630, from which the processing unit 620 receives and executes instructions. The data received by the system memory 630 can optionally be stored on the removable storage 640 or the non-removable storage 650 before or after execution by the processing unit 620.

The computing device 600 typically includes a variety of computer-readable media. Computer-readable media can be any available media that can be accessed by device 600 and includes both volatile and non-volatile media, removable and non-removable media. Computer storage media include volatile and non-volatile, and removable and non-removable media implemented in any method or technology for storage of information such as computer readable instructions, data structures, program modules or other data. System memory 630, removable storage 640, and non-removable storage 650 are all examples of computer storage media. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 600. Any such computer storage media can be part of computing device 600.

It should be understood that the various techniques described herein can be implemented in connection with hardware or software or, where appropriate, with combinations thereof. Thus, the methods, systems, and associated signal processing of the presently disclosed subject matter, or certain aspects or portions thereof, can take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs can implement or utilize the processes described in connection with the presently disclosed subject matter, e.g., through the use of an application programming interface, reusable controls, or the like. Such programs can be implemented in a high level procedural or object-oriented programming language to communicate with a computer system. However, the program(s) can be implemented in assembly or machine language, if desired. In any case, the language can be a compiled or interpreted language and it may be combined with hardware implementations.

Also disclosed herein are computing devices comprising a processor and a memory operably coupled to the processor, the memory having further computer-executable instructions stored thereon that, when executed by the processor, cause the processor to: receive an electrochemical signal produced by any of the devices or methods described herein; process the electrochemical signal to detect the analyte (e.g., determine the concentration of the analyte). In some examples, the analyte can comprise a biomarker and the computer-executable instructions stored on the memory that, when executed by the processor, can further cause the processor to correlate the presence and/or concentration of the biomarker with a risk factor, presence, and/or progress of a disease in a subject (e.g., detect or monitor a disease in a subject). In certain examples, the computer-executable instructions stored on the memory that, when executed by the processor, can further cause the processor to output the presence and/or concentration of the biomarker; the risk factor, presence, and/or progress of the disease; or a combination thereof. For example, the results can be output to an output device (e.g., a display, printer, etc.) and/or the results can put output to an electronic health record of the subject and optionally stored in said electronic health record.

Embodiments of the methods and systems may be described herein with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

The devices and methods described herein are inexpensive, user friendly (e.g., they can provide for electrochemical detection without any washing steps), sensitive, portable, robust (they employ metal particles for signal amplification as opposed to enzymes), efficient, rapid, and can detect low concentrations (e.g., low picomolar to low femtomolar concentrations of analyte). As such, the device and methods are well suited for use in numerous sensing applications.

For example, the devices and methods described herein can be used in clinical and healthcare settings to detect and/or quantify biomarkers to identify risk for, diagnosis of, or progression of a pathological or physiological process in a subject. Examples of biomarkers include proteins, peptides, polypeptides, hormones, prohormones, lipids, carbohydrates, DNA, RNA, and combinations thereof.

The devices and methods described herein can be used in POC applications to diagnose infections in a patient (e.g., by measuring serum antibody concentrations or detect antigens). For example, the devices and methods described herein can be used to diagnose viral infections (e.g., HIV, hepatitis B, hepatitis C, rotavirus, influenza, polio, measles, yellow fever, rabies, dengue, or West Nile Virus), bacterial infections (e.g., *E. coli, C. tetani*, cholera, typhoid, diphtheria, tuberculosis, plague, Lyme disease, or *H. pylori*), and parasitic infections (e.g., toxoplasmosis, Chagas disease, or malaria). The devices and methods described herein can be used to rapidly assesses the immune status of people or animals against selected vaccine-preventable diseases (e.g. anthrax, human papillomavirus (HPV), diphtheria, hepatitis A, hepatitis B, *Haemophilus influenzae* type b (Hib), influenza (flu), Japanese encephalitis (JE), measles, meningococcal, mumps, pertussis, pneumococcal, polio, rabies, rotavirus, rubella, shingles (herpes zoster), smallpox, tetanus, typhoid, tuberculosis (TB), varicella (chickenpox), yellow fever). The devices and methods described herein can be used to rapidly screen donated blood for evidence of viral contamination by HIV, hepatitis C, hepatitis B, and HTLV-1 and -2. The devices and methods described herein can also be used to measure hormone levels. For example, the devices and methods described herein can be used to measure levels of human chorionic gonadotropin (hCG) (as a test for pregnancy), Luteinizing Hormone (LH) (to determine the time of ovulation), or Thyroid Stimulating Hormone (TSH) (to assess thyroid function). The devices and methods described herein can be used to diagnose or monitor diabetes in a patient, for example, by measuring levels of glycosylated hemoglobin, insulin, or combinations thereof. The devices and methods described herein can be used to detect protein modifications (e.g., based on a differential charge between the native and modified protein and/or by utilizing recognition elements specific for either the native or modified protein). The devices and methods described herein can be used to administer personalized medical therapies to a subject (e.g., in a pharmacogenomic assay performed to select a therapy to be administered to a subject) or as companion diagnostics for therapeutic agents (e.g. in a therapeutic regimen to determine the correct dosage or to identify iatrogenic effects).

More than 5 million individuals in the U.S. suffer from clinically manifest heart failure (HF), and that number continues to rise with the country's aging population, contributing to strains on the healthcare system and to economic costs. Diagnosing and managing the cardiovascular health concerns for such a large population has created a growing need for new healthcare technologies that will help accommodate the physical challenges of aging HF patients and lower medical cost and the strain on healthcare resources.

Elevated blood concentrations of certain natriuretic peptides can indicate the presence of myocardial stress, and in people with heart failure the concentration of these biomarkers can correlate with acute exacerbations of this condition (i.e., heart failure). As used herein, natriuretic peptides include N-terminal pro-brain natriuretic peptide (NT-proBNP), B-type natriuretic peptide (BNP, also known as brain natriuretic peptide), atrial natriuretic peptide (ANP), derivatives thereof, and combinations thereof. NT-proBNP and BNP levels in blood can be tested clinically to detect and evaluate heart failure.

BNP is a 32-amino-acid-ringed peptide that functions in the body as a hormone to regulate blood pressure. BNP is produced primarily in the left ventricle of the heart, where it is stored under normal conditions, and is released into the bloodstream when the heart is stressed by stretching, volume expansion, or high pressure, such as when the heart is working hard to pump blood, as occurs in patients with heart failure. Pro-BNP is a precursor protein that is produced by the heart and then cleaved by an enzyme, which releases into the blood both the active BNP hormone and an inactive fragment, NT-proBNP. Compared to BNP, NT-proBNP has a longer circulatory half-life (60-90 minutes vs. 20 minutes), a higher clinical cut-off point, and greater predictive value for 90-day post-discharge mortality predictive value. BNP, however, is more routinely measured clinically.

Quantitation of natriuretic peptide levels can be used to determine appropriate emergency and clinical treatment, and it is currently the only blood-based assay that exists for the diagnosis of myocardial stress and management of heart failure. Studies where natriuretic peptides were used to guide drug therapies and diagnostics suggest reduced mortality and a significantly lowered number and duration of hospital stays. This simple, effective means of monitoring and diagnosis of cardiovascular health, combined with a technologically accurate and demographically relevant means of testing for a robust heart failure biomarker, presents an opportunity to provide support for the growing population of aging heart failure patients. Accordingly, in some examples, the devices and methods described herein can be used to diagnose and/or monitor heart failure (HF) in a subject by measuring levels of a biomarker. In certain examples, the devices and methods described herein can be used to diagnose and/or monitor heart failure (HF) in a subject, for example, by measuring levels of BNP, proBNP, or combinations thereof.

In some examples, the devices and methods described herein can be used to diagnose and/or monitor heart failure (HF) in a subject, for example, by measuring levels of BNP, proBNP, or combinations thereof in the blood of the subject, wherein the concentration of NT-proBNP or BNP in blood of the subject is 50 picomolar (pM) or more (e.g., 75 pM or more, 100 pM or more, 125 pM or more, 150 pM or more, 175 pM or more, 200 pM or more, or 225 pM or more). In some examples, the devices and methods described herein can be used to diagnose and/or monitor heart failure (HF) in a subject, for example, by measuring levels of BNP, proBNP, or combinations thereof in the blood of the subject, wherein the concentration of NT-proBNP or BNP in blood of the subject is 250 pM or less (e.g., 225 pM or less, 200 pM or less, 175 pM or less, 150 pM or less, 125 pM or less, 100 pM or less, or 75 pM or less). The concentration of NT-proBNP or BNP in blood of the subject measured by the devices or methods described herein can range from any of the minimum values described above to any of the maximum values described above. For example, the devices and methods described herein can be used to diagnose and/or monitor heart failure (HF) in a subject, for example, by measuring levels of BNP, proBNP, or combinations thereof in the blood of the subject, wherein the concentration of NT-proBNP or BNP in blood of the subject is in the range of from 50 pM to 250 pM (e.g., from 50 pM to 150 pM, from 150 pM to 250 pM, from 50 pM to 100 pM, from 100 pM to 150 pM, from 150 pM to 200 pM, from 200 pM to 250 pM, or from 75 pM to 225 pM).

Weight gain in subjects with heart failure is a well-known and traditionally used marker of decompensation, and researchers have suggested that patient weight increase is a risk factor for imminent heart failure hospitalization (Chaudhry et al, 2007 *Circulation*). Consequently, weight gain from edema forms a foundational part of a clinician's examination and subsequent decisions regarding management, care and therapy for a subject with heart failure. However, for more advanced stages of heart failure, a second condition can arise, known as cachexia. Cachexia is a wasting syndrome in which loss of weight, muscle atrophy and significant loss of appetite occurs, resulting in loss of lean body mass that cannot be reversed nutritionally. Co-morbidity of heart failure and cachexia can lead to a situation where the patient is decompensating and experiencing edema and shortness of breath, but fails to exhibit weight gain as a consequence of the effects of cachexia. Elevated natriuretic peptide levels for either BNP or NT-proBNP can allow a clinician to detect developing decompensation even in the situation where worsening edema was confounded by concurrent cachexia.

Figure 16:
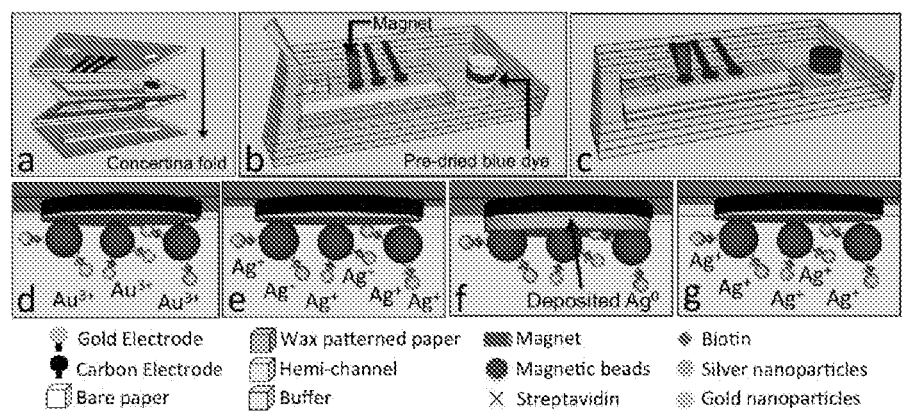
FIG. 16 illustrates the NoSlip paper sensor design and functionality. Panel (a) shows assembling the device via concertina folding. Panel (b) shows loading the composite solution at the inlet of the assembled device with the magnet place on the top of the working electrode to concentrate the composite. Panel (c) shows that the solution fills the device causing the outlet indicator to turn blue. Panels (d)-(g) show cross-sectional views of the hollow channel in an area next to the working electrode (WE), showing how the galvanic exchange electrochemical detection method is performed.
Figure 17:
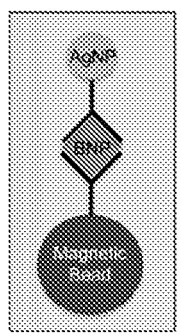
FIG. 17 illustrates the sandwich structure formed by the antibody modified silver nanoparticle and antibody modified magnetic bead binding to the target, for example BNP.

An example embodiment of the methods and devices describes herein will now be described. As shown in FIG. 16, a sample (for example, a finger-stick blood sample with a volume of approximately 10-50 µL) is applied to the Inlet. Silver nanoparticles (AgNPs) are modified with one antibody for the target (tAb), and magnetic microbeads (MµBs) are modified with another antibody (cAb). Both the modified silver nanoparticles and modified magnetic microbeads are predisposed on the device, and these are resolvated by the blood sample. If the target (for example, a natriuretic peptide, preferably BNP or NT-proBNP) is present, the target can form a sandwich of the type shown, for example, in FIG. 17. The sample matrix containing this sandwich now flows down the hollow channel, but the magnetic microbeads are captured by the magnetic field of the magnet and held immediately adjacent to the working electrode. Some of the silver nanoparticles, in an amount proportional to the amount of target present, due to the formation of the sandwich with the target, are also captured by the magnetic field of the magnet and held immediately adjacent to the working electrode. Any silver nanoparticles not bound to magnetic microbeads by at least one target molecule are free to flow past the working electrode. In certain examples, no pump is required as flow may be driven by capillary action. When the entire sample has flowed past the working electrode (which, for example, can be signaled by the appearance of a colored dye at the outlet), an appropriate electrochemical waveform is applied to the working electrode that results in deposition of any adjacent silver nanoparticles onto its surface. The current corresponding to oxidation of the silver, which is proportional to the target concentration, is then measured by the reader. Because a 20 nm silver nanoparticle can provide 250,000 equivalents of electrons, the presence of each target molecule can be amplified 250,000 times.

The devices and methods described herein can also be used in other commercial applications. For example, the devices and methods described herein can be used in the food and beverage industry, for example, in quality control applications or to detect potential food allergens, such as milk, peanuts, walnuts, almonds, eggs, gluten, or combinations thereof. The devices and methods described herein can be used in the food and beverage industry, for example, in quality control applications or to detect potential foodborne pathogens, such as *Campylocavter jejuni, Clostridium botulinum, Clostridium perfringens*, pathogenic *Escherichia coli* (*E. coli*), *Listeria monocytogenes, Norovirus, Salmonella Enteritidis, Salmonella Typhimurium, Shigella, Satphylococcus aureus, Vibrio cholerea, Vibrio parahaemolyticus, Vibria vulnificus, Yersinia enterocolitica*, or combinations thereof. The devices and methods described herein can be used to detect and/or measure the levels of proteins of interest in foods, cosmetics, nutraceuticals, pharmaceuticals, and other consumer products. The devices and methods described herein can also be used to rapidly and accurately detect narcotics and biothreat agents (e.g., ricin).

Also disclosed herein are kits that comprise the devices disclosed herein in one or more containers. In some embodiments, the kit can comprise a kit for diagnosing and/or monitoring heart failure in a subject. In certain embodiments, the kit can further comprise a recognition element bound to the magnetic particle; and a recognition element bound to the particle formed from the first metal. In certain embodiments, the recognition element bound to the magnetic particle can comprise a recognition element for N-terminal pro-brain natriuretic peptide (NT-proBNP) and/or B-type natriuretic peptide (BNP). In certain embodiments, the recognition element bound to the particle formed from the first metal can comprise a recognition element for N-terminal pro-brain natriuretic peptide (NT-proBNP) and/or B-type natriuretic peptide (BNP) In one embodiment, a kit includes one or more other components, adjuncts, or adjuvants. In one embodiment, a kit includes instructions or packaging materials that describe how to use the device of the kit. Containers of the kit can be of any suitable material, e.g., glass, plastic, metal, etc., and of any suitable size, shape, or configuration.

The examples below are intended to further illustrate certain aspects of the systems and methods described herein, and are not intended to limit the scope of the claims.

Examples

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures and other reaction ranges and conditions that can be used to optimize the product purity and yield obtained from the described process.

Background

In the past 10 years the scientific community has seen a burgeoning interest in the development of paper point-of-care (POC) devices that are cheap, user friendly, robust, sensitive, and portable. Such devices pose an effective solution to the existing economic and healthcare accessibility problems in underdeveloped countries, as well as the growing trend in more affluent societies to become better informed in terms of their health. Although commercial paper-like sensors have been around for about 25 years (e.g., pregnancy test and glucose test strips), few paper POC devices have been successfully commercialized. Such failure to produce trustworthy paper POC devices is a combination of many factors, including poor limits of detection, non-specific adsorption, robustness of the reagents used, sensitivity of the method, time for completion of analysis, complex user-technology interface, and technically-demanding detection methods.

The type of detection method used is important because the output signal needs to be easily understood by the user and detectable in the field. Electrochemistry and colorimetry have been widely used for detection because of the nature of their signal. However, electrochemistry has surpassed colorimetry because it can achieve superior analytical performance and there is technology already available that facilitates the use of inexpensive instrumentation (e.g., <$80). The electrochemical sensors with the lowest limits of detection found in the literature involve the use of enzymes (which, however, are very sensitive to environmental changes, salt concentrations, and solvents and usually require the presence of a cofactor and mediators for acceptable functionality) and complicated electrode manufacturing for the amplification of the desired signal (Wu Y et al. *Anal. Chem.* 2013, 85, 8661-8668; Feng Q M et al. *Talanta* 2013, 115, 235-240). Often, these factors limit the applicability of such devices to only a few analytes and conditions.

Overview

Described herein are methods and devices that comprise integrating a robust electrochemical process (galvanic exchange) with a metal nanoparticle based immunoassay. Commercially available silver nanoparticles (AgNPs, 20 nm diameter, from Ted Pella, Redding, Calif.) were functionalized with biotin and then bound to commercially available magnetic microbeads functionalized with streptavidin (2.8 ~µm in diameter, from Bangs Laboratories, Fishers, Ind.). The resulting AgNP/biotin/streptavidin/magnetic microbead composite was injected into the paper device and concentrated via a magnet (present in the device holder) next to the device's electrode. It is at the electrode wherein the signal resulting from the AgNPs can be detected. However, as is, the composite does not provide a high signal because AgNPs are next to an insulating surface (e.g., the magnetic microbeads). In order for the Ag contained in each AgNP to be detected, there has to be good electrical contact between each AgNP and the electrode. This problem has been previously solved both in a paper fluidic platforms (Scida K et al. *Anal. Chem.* 2014, 86, 6501-6507) and in a bulk solution system (Authier L et al. *Anal Chem.* 2001, 73, 4450-4456) by using a strong oxidizing agent to dissolve the AgNP tags into Ag ions. These Ag ions are then electrodeposited onto the electrode's surface; therefore, all the Ag ions that were previously in the form of AgNPs in the composite are now free to make direct electrical contact with the electrode.

The devices and methods described herein provide a more selective, simple, and stable way to oxidize AgNPs to $Ag^+$ in comparison to the conventional chemical oxidants. Specifically, the galvanic exchange oxidation includes two steps. First, in situ electro-generation of $Au^{3+}$ occurs at a gold-coated carbon electrode. Second, $Au^{3+}$ galvanically exchanges with AgNPs, which results in $Au^0$ and oxidized Ag+. One of the benefits for using galvanic exchange to oxidize silver is that $Au^{3+}$ is a mild oxidant that is stable indefinitely (in the form of $Au^0$) and will exclusively oxidize AgNPs in a controlled manner near the electrode surface. In contrast, chemical oxidants have a short shelf life, are difficult to prepare for manufacturing and storage purposes, and may detrimentally exert their non-specific oxidative effects on the other reagents and materials of the device. Herein, the galvanic exchange technique is demonstrated using a model AgNP/biotin/streptavidin/magnetic microbead composite on a paper fluidic platform (referred to herein as the "NoSlip" device). This technique is applicable to various analytes (e.g. biomarkers such as proteins, peptides, polypeptides, hormones, prohormones, lipids, carbohydrates, DNA, RNA, or combinations thereof; viral particles; or bacteria) and electrochemical setups.

Experimental

Figure 15:
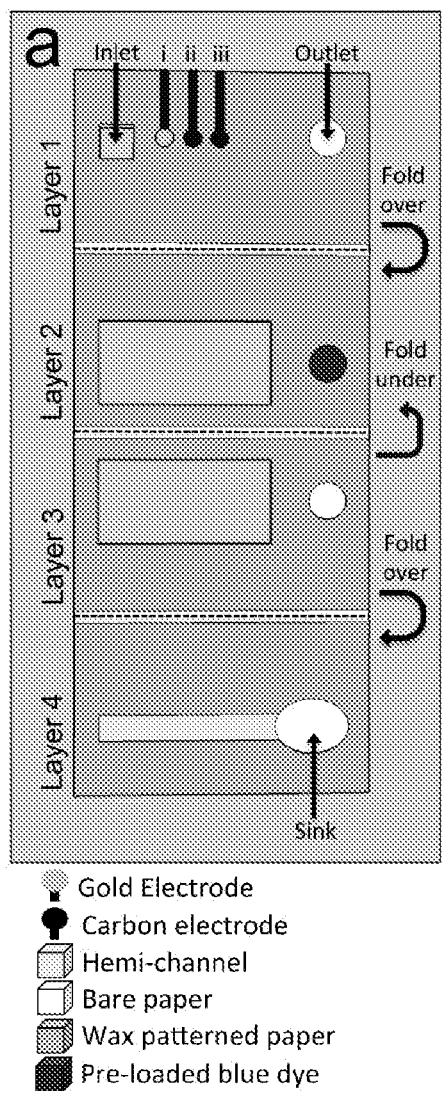
FIG. 15 illustrates the design of the unassembled NoSlip origami paper-based analytical device.

A schematic of the NoSlip paper device is shown in FIG. 15. The sensor platform is composed of four wax-printed paper layers, fabricated from a single piece of paper, and subsequently folded to form the working device. Layer 1 has two reservoirs, the inlet and the outlet. The inlet has its cellulose content removed and the outlet can contain cellulose. In addition, stencil-printed carbon electrodes are fabricated on the lower face of this layer (e.g., the face in contact with layer 2 in the assembled device). In FIG. 15, the electrodes from the left to the right refer to the (i) working electrode (WE), (ii) reference electrode (RE), and (iii) counter electrode (CE), respectively. The WE has gold pre-deposited on the surface of the carbon electrode, which will be later used for the galvanic exchange. Layers 2 and 3 contain a hollow channel, and layer 2 has a paper reservoir loaded with a blue dye, which is later used to signal when flow is complete. Layer 4 consists of a hydrophilic layer (a hemichannel) and a sink pad that drives a continuous flow of fluid through the device until the sink has filled with fluid. The NoSlip is assembled by folding the paper as instructed in FIG. 15 and FIG. 16, panel a, to create an origami-based three-dimensional paper device.

The general operation of the NoSlip is shown in FIG. 16. Once the device is assembled, the sample is loaded at the inlet with the magnet placed above the WE (FIG. 16, panel b), resulting in localization of the composite. Flow is driven through the hollow channel (layer 2 and 3) and hemichannel (layer 4) by capillary forces in the hemi-channel. As the sink pad becomes full, upward flow is initiated through the paper reservoir at the right end of layer 3. This upward flow rehydrates the preloaded blue dye on layer 2 and causes the outlet on layer 1 to turn blue. When the outlet turns blue it indicates that flow is complete (FIG. 16, panel c) and the galvanic exchange detection method can be initiated.

FIG. 16 panels d-g illustrate what occurs when the sample reaches the WE. When the flow is complete, the composites (AgNP bound to magnetic bead, for example, through the streptavidin-biotin specific interaction or a specific interaction between NT-proBNP and anti-NT-proBNP) are concentrated at the WE via the magnet. The pre-deposited gold ($Au^0$) is electro-oxidized off the WE to generate $Au^{3+}$ in a localized manner by chronopotentiometry (FIG. 16, panel d). Next, galvanic exchange between $Au^{3+}$ and $Ag^0$ takes place spontaneously, because Au is more noble than Ag. The AgNPs ($Ag^0$) specifically exchange with $Au^{3+}$ to form $Au^0$ (gold nanoparticles) and $Ag^+$ ($3Ag_{(s)} + Au^{3+}_{(aq)} \rightarrow 3 Ag^+_{(aq)} + Au_{(s)}$) (FIG. 16, panel e). These Ag ions are then electrodeposited onto the electrode surface (FIG. 16, panel f) by holding the WE at a reducing potential of −0.7 V vs. carbon quasi-reference electrode (CQRE) for 200 s. Therefore, all $Ag^+$ that was previously in the form of AgNPs in the composite becomes $Ag^0$ in direct electrical contact with the electrode. In the absence of galvanic exchange, no Ag signal is observed at high Ag concentrations. Finally, $Ag^0$ is electrochemically stripped off the WE by oxidizing Ag to $Ag^+$ (for example, at a scan rate in the range of 1-100 mV/s (e.g., in the range 10-80 mV/s or at a scan rate of 60 mV/s), and a sweeping potential from −0.7 to 0.2 V vs CQRE), yielding a quantitative signal by integration of the current-time transient peak. The resulting charge reflects the number of AgNPs present in the composite in this model assay, and, hence in, for example, a sandwich immunoassay, the concentration of the desired analyte, for example NT-proBNP. In a model assay, the biotin-labeled silver nanoparticle tags form the composite with streptavidin-functionalized magnetic microbeads to allow magnetic concentration of the specific binding events and to electrochemically amplify the quantitative signal of each binding event. In a NT-proBNP assay, silver nanoparticle tags labeled with anti-NT-proBNP can form the composite with anti-NT-proBNP functionalized magnetic microbeads bound to the target analyte, NT-proBNP. Magnetic concentration and electrochemical amplification are conducted in the same manner for the NT-proBNP assay as they are for the model assay. Each 20 nm AgNP contains 250,000 silver atoms, which corresponds to an amplification factor of $2.5 \times 10^5$ for every AgNP. Furthermore, amplification is increased through the localization, and thereby concentration, of the composites containing AgNP tags at the WE via a magnet on the paper device.

Figure 18:
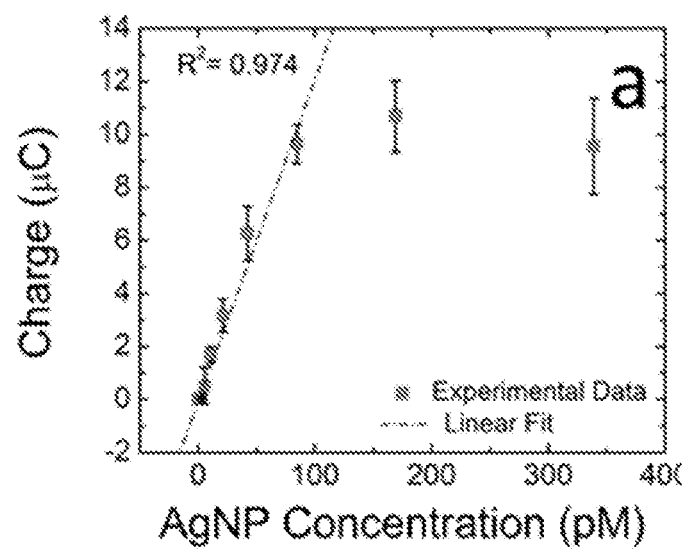
FIG. 18 displays the dose response curve for the model AgNP/biotin/streptavidin/magnetic microbead composite in buffer using the NoSlip device and galvanic exchange detection method (panel a) and the associated anodic stripping voltammograms for the various model composite concentrations (panel b).
Figure 18:
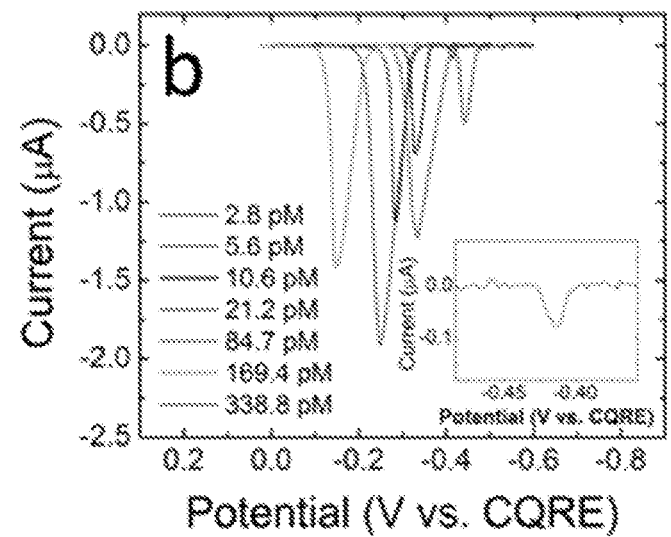
Figure 19:
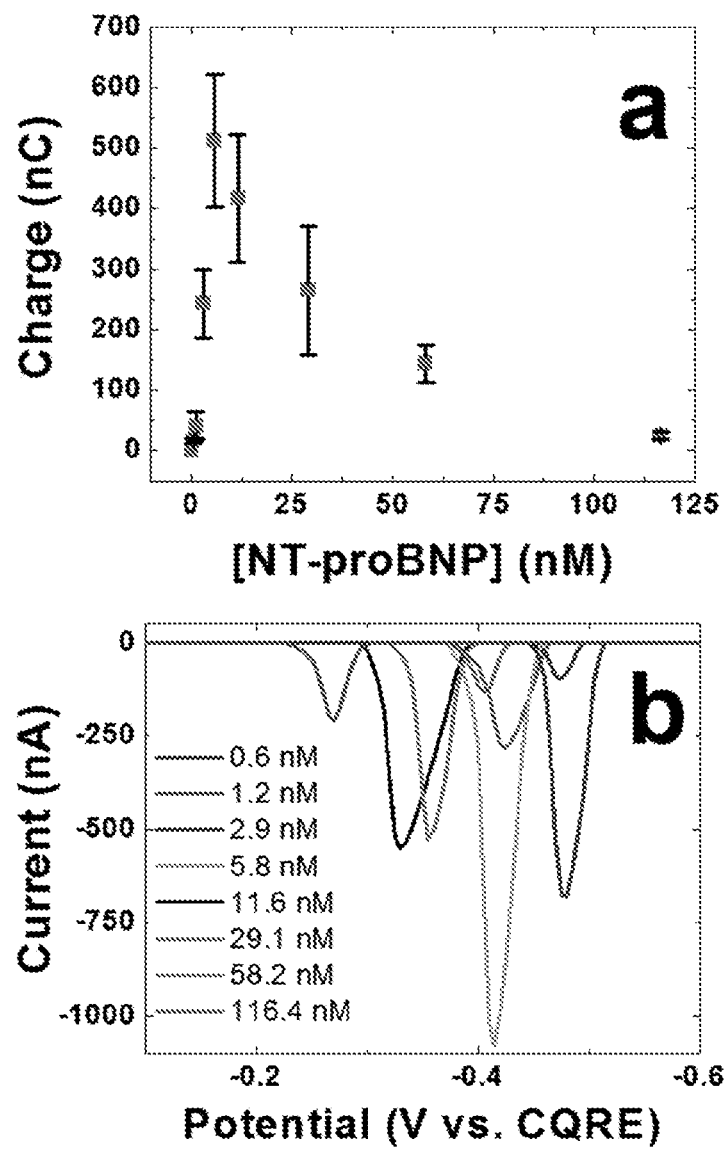
FIG. 19 displays the dose response curve for the model AgNP/anti-NT-proBNP/NT-proBNP/anti-NT-proBNP/magnetic microbead composite in buffer using the NoSlip device and galvanic exchange detection method (panel a) and the associated anodic stripping voltammograms for the various model composite concentrations (panel b).

A dose response curve for the model AgNP/biotin/streptavidin/magnetic microbead composite in buffer is shown in FIG. 18, panel a, and the associated anodic stripping voltammograms are shown in FIG. 18, panel b. With this method, 2.5 pM AgNPs present in the composite were detected with a collection efficiency of 16.8%, a pre-prototype device-to-device coefficient of variation of 15.6%, good sensitivity, and signal output in 6 min. A dose response curve for the AgNP/anti-NT-proBNP/NT-proBNP/anti-NT-proBNP/magnetic microbead composite in buffer is shown in FIG. 19, panel a, and the associated anodic stripping voltammograms are shown in FIG. 19, panel b. With this method, 582 pM NT-proBNP were detected with a device-to-device coefficient of variation of 29.7%, good sensitivity, and signal output in 6 min. This sensor can be configured to detect a variety of target molecules, such as biomarkers (e.g., proteins, peptides, polypeptides, hormones, prohormones, lipids, carbohydrates, DNA, RNA, and combinations thereof), bacteria, viruses, etc., because the AgNPs and magnetic microbeads can be functionalized with many other binding agents (e.g., antibodies, aptamers, or DNA) in order to build, for example, a sandwich type assay, without changing the source of the signal or the signal amplification method.

Figure 20:
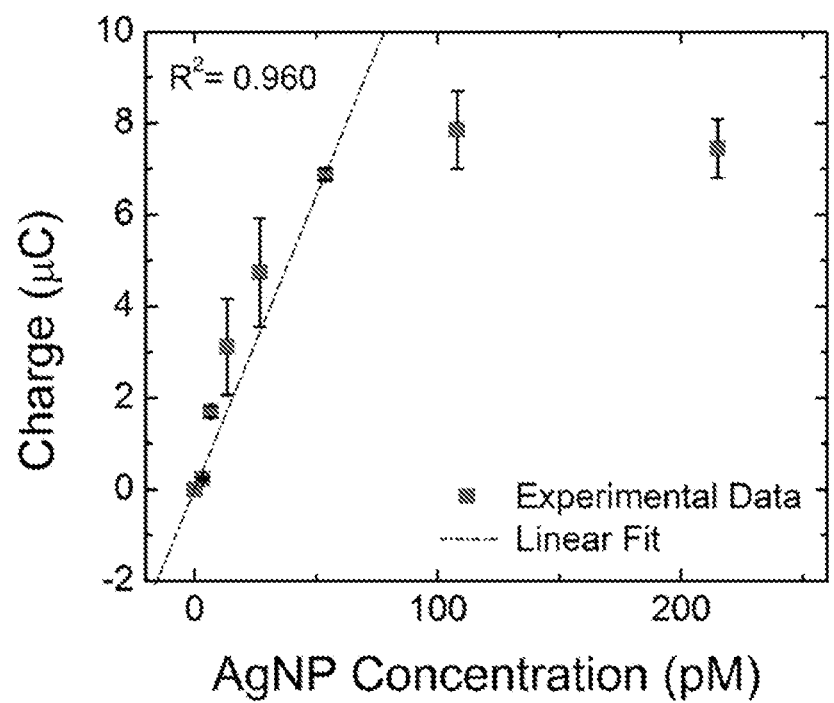
FIG. 20 displays the dose response curve for the model AgNP/biotin/streptavidin/magnetic microbead composite in artificial urine using the NoSlip device and galvanic exchange detection method.

Since this galvanic exchange is very specific between the Au at the WE and the AgNP, detection can be done in complex matrices, such as urine. Also, by using chronopotentiometry, the potential applied can be automatically adjusted to account for interfering species within the matrix, such as chloride in urine. A dose response curve for the model AgNP/biotin/streptavidin/magnetic microbead composite is shown in FIG. 20. Even in this more complex matrix, the galvanic exchange method was able to detect 1.7 pM of AgNPs present in the composite.

What is claimed is:

1. A device for the detection of an analyte conjugated to a magnetic particle and a particle formed from a first metal, the device comprising:
   a channel defining a path for fluid flow from a fluid inlet to a fluid outlet;
   a working electrode positioned in electrochemical contact with a region of the channel, wherein the working electrode comprises a second metal, and wherein the second metal has a higher reduction potential than the first metal; and
   a magnet configured to apply a magnetic field to the region of the channel in electrochemical contact with the working electrode.

2. A method for detecting an analyte comprising:
   a. flowing fluid along a channel to accumulate the analyte conjugated to a particle formed from a first metal in a region of the channel in electrochemical contact with a working electrode, wherein the analyte conjugated to the particle formed from the first metal is accumulated in the region of the channel by a localization element;
   b. galvanically exchanging the first metal with ions of a second metal, thereby forming a layer of the first metal at the working electrode; and
   c. electrochemically detecting the first metal, wherein the localization element is selected from the group consisting of a physical barrier disposed in the region of the channel, a localization electrode configured to apply an electric field to the region of the channel, a magnet configured to apply a magnetic field to the region of the channel, or a combination thereof.

3. The method of claim 2, wherein electrochemically detecting the first metal comprises electrochemically oxidizing the first metal to quantify the amount of the first metal in the layer at the working electrode.

4. The method of claim 2, wherein electrochemically detecting the first metal comprises quantifying the concentration of the analyte.

5. The method of claim 2, wherein the analyte is bound to the particle of the first metal by a recognition element.

6. The method of claim 2, wherein the channel defines a path for fluid flow from a fluid inlet to a fluid outlet, and wherein the method further comprises injecting a sample comprising a molecule of interest into the fluid inlet.

7. The method of claim 6, wherein the molecule of interest is the analyte.

8. The method of claim 6, wherein the analyte comprises a surrogate for the molecule of interest.

9. The method of claim 8, wherein the surrogate is conjugated to a fixed analyte support, the particle formed from the first metal, the magnetic particle, or combinations thereof, and wherein the surrogate is displaced by the molecule of interest.

10. The method of claim 2, wherein the working electrode comprises the second metal.

11. The method of claim 10, wherein the method further comprises electrochemically oxidizing the second metal to provide the ions of the second metal.

12. The method claim 2, wherein the method further comprises providing a source of the ions of the second metal to the region of the channel, wherein the source of the ions of the second metal is a compound comprising the second metal.

13. The method of claim 2, wherein the analyte comprises an analyte conjugated to a particle formed from a first metal and a magnetic particle, and wherein the localization element comprises a magnet configured to apply a magnetic field to the region of the channel.

14. The method of claim 13, wherein the analyte is bound to the magnetic particle by a recognition element.

15. The method of claim 13, wherein step (a) comprises flowing fluid comprising the analyte conjugated to the particle formed from the first metal and the magnetic particle along the channel, and applying the magnetic field to accumulate the analyte conjugated to the particle formed from the first metal and the magnetic particle in the region of the channel.

16. The method of claim 2, wherein the analyte is charged, and wherein the localization element comprises a localization electrode configured to apply an electric field to the region of the channel.

17. The method of claim 16, wherein step (a) comprises flowing fluid comprising the charged analyte conjugated to the particle formed from the first metal along the channel, and applying an electric field to accumulate the charged analyte conjugated to the particle formed from the first metal in the region of the channel.

18. The method of claim 2, wherein the localization element comprises a physical barrier disposed in the region of the channel, and wherein step (a) comprises flowing fluid comprising the analyte conjugated to the particle formed from the first metal along the channel to contact the physical barrier such that the analyte conjugated to the particle formed from the first metal accumulates in the region of the channel.

19. The method of claim 2, wherein the analyte is selected from the group consisting of antibodies, peptides, proteins, polynucleotides, lipids, polysaccharides, small molecule organic compounds, pathogens, and combinations thereof.

20. The method of claim 19, wherein the analyte comprises a natriuretic peptide.

21. The method of claim 20, wherein the natriuretic peptide is selected from the group consisting of N-terminal pro-brain natriuretic peptide (NT-proBNP), B-type natriuretic peptide (BNP), and combinations thereof.

22. The method of claim 2, wherein the analyte comprises a biomarker indicative of a disease.

23. A method for detecting an analyte by galvanic exchange, the method comprising:
   a. providing an analyte conjugated to a particle formed from a first metal;
   b. galvanically exchanging the first metal with ions of a second metal, thereby forming a product of the galvanic exchange; and
   c. detecting the product of the galvanic exchange.

24. The method of claim 23, wherein the product of the galvanic exchange comprises a plurality of particles formed from the second metal.

* * * * *